United States Patent
Puder et al.

(10) Patent No.: US 8,951,550 B2
(45) Date of Patent: *Feb. 10, 2015

(54) DIETARY FORMULATIONS AND METHODS FOR TREATMENT OF INFLAMMATION AND OTHER DISORDERS

(71) Applicants: Children's Medical Center Corporation, Boston, MA (US); Beth Israel Deaconess Medical Center, Inc., Boston, MA (US)

(72) Inventors: Mark Puder, Medfield, MA (US); Bruce Bistrian, Ipswich, MA (US)

(73) Assignees: Children's Medical Center Corporation, Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/148,197

(22) Filed: Jan. 6, 2014

(65) Prior Publication Data
US 2014/0194511 A1  Jul. 10, 2014

Related U.S. Application Data

(63) Continuation of application No. 12/602,054, filed as application No. PCT/US2008/006691 on May 27, 2008, now Pat. No. 8,652,508.

(60) Provisional application No. 60/931,888, filed on May 25, 2007.

(51) Int. Cl.
| | | |
|---|---|---|
| A61K 47/00 | (2006.01) | |
| A23D 9/013 | (2006.01) | |
| A23L 1/30 | (2006.01) | |
| A61K 31/202 | (2006.01) | |
| A61K 31/23 | (2006.01) | |

(52) U.S. Cl.
CPC .............. *A23D 9/013* (2013.01); *A23L 1/3008* (2013.01); *A61K 31/202* (2013.01); *A61K 31/23* (2013.01); *A23V 2002/00* (2013.01)
USPC ........................................................ 424/439

(58) Field of Classification Search
None
See application file for complete search history.

(56) References Cited

U.S. PATENT DOCUMENTS

| | | | |
|---|---|---|---|
| 4,820,731 A | 4/1989 | Mascioli et al. | |
| 5,661,180 A | 8/1997 | De Michele et al. | |
| 5,993,221 A | 11/1999 | Bistrian | |
| 6,080,787 A | 6/2000 | Carlson et al. | |
| 7,045,143 B1 | 5/2006 | Sawatzki et al. | |
| 2008/0275119 A1 | 11/2008 | Puder et al. | |

FOREIGN PATENT DOCUMENTS

| | | |
|---|---|---|
| EP | 1279400 A | 1/2003 |
| WO | 02/13838 A | 2/2002 |
| WO | 2005/046669 A | 11/2009 |

OTHER PUBLICATIONS

Edwards H. et al., The J. of Nutrition, 81:123-180 (Oct. 1963)—XP002515312.
Gura, K. et al., Clinical Nutrition (Edinburgh, Scotland) 24:839-847 (Oct. 2005)—XP002515773.
Privett, OS et al., The J. of Nutrition, 71:66-69 (May 1960)—XP002515772.
Alwayn IP et al. "Omega-3 fatty acid supplementation prevents hepatic steatosis in a murine model of nonalcoholic fatty liver disease," Pediatr Res. 57(3):445-452 (Mar. 2005).
Bistrian BR "Clinical aspects of essential fatty acid metabolism: Jonathan Rhoads Lecture," JPEN J Parenter Enteral Nutr. 27(3):168-175 (May-Jun. 2003).
Bjerve KS et. al., "Alpha-linolenic acid deficiency in man: effect of ethyl linolenate on plasma and erythrocyte fatty acid composition and biosynthesis of prostanoids," Am J Clin Nutr. 46(4):570-576 (Oct. 1987).
Bjerve KS et al. "Alpha-Linolenic acid and long-chain omega-3 fatty acid supplementation in three patients with omega-3 fatty acid deficiency: effect on lymphocyte function, plasma and red cell lipids, and prostanoid formation," Am J Clin Nutr. 49(2):290-300 (Feb. 1989).
Bjerve KS et al. "Alpha-linolenic acid deficiency in patients on long-term gastric-tube feeding: estimation of linolenic acid and long-chain unsaturated n-3 fatty acid requirement in man," Am J Clin Nutr. 45(1):66-77 (Jan. 1987).
Carlson SE et al. "First year growth of preterm infants fed standard compared to marine oil n-3 supplemented formula," Lipids. 27(11):901-907 (Nov. 1992).
Carlson SE et al. "Arachidonic acid status correlates with first year growth in preterm infants," Proc Natl Acad Sci U S A. 90(3):1073-1077 (Feb. 1, 1993).

(Continued)

*Primary Examiner* — Robert A Wax
*Assistant Examiner* — Olga V Tcherkasskaya
(74) *Attorney, Agent, or Firm* — Shayne Y. Huff; David S. Resnick; Nixon Peabody LLP

(57) ABSTRACT

Dietary formulations in the form of an oil emulsion providing total enteral or parenteral nutrition, or in the form of food oil suitable for oral administration is provided. The formulations include about 2-60% by calories of a $C_{20}$ or longer omega-3 fatty acid and about 0.05% to 1% by calories of arachidonic acid, where the formulation provides less than 1% of total calories from linoleic acid and alpha-linolenic acid, and where the fatty acids provide 5-60% of the total calories of said dietary formulation. Methods for treatment of diseases and disorders using the dietary formulations are also provided.

1 Claim, 14 Drawing Sheets

(56) References Cited

OTHER PUBLICATIONS

Carlson SE et al. "Effect of long-chain n-3 fatty acid supplementation on visual acuity and growth of preterm infants with and without bronchopulmonary dysplasia," Am J Clin Nutr. 63(5):687-697 (May 1996).

Carter BA et al. "Mechanisms of disease: update on the molecular etiology and fundamentals of parenteral nutrition associated cholestasis," Nat Clin Pract Gastroenterol Hepatol. 4(5):277-287 (May 2007).

Carter BA et al. "Stigmasterol, a soy lipid-derived phytosterol, is an antagonist of the bile acid nuclear receptor FXR," Pediatr Res. 62(3):301-306 (Sep. 2007).

Chen WJ et al. "Effects of fish oil in parenteral nutrition," Nutrition. 19(3):275-279 (Mar. 2003).

Cunnane SC "Problems with essential fatty acids: time for a new paradigm?" Prog Lipid Res. 42(6):544-568 (Nov. 2003).

DAS. Essential fatty acids: biochemistry, physiology and pathology. Biotechnology Journal. 420-439 (Mar. 6, 2006).

Lupton, J.R. et al. Dietary Reference Intakes for Energy, Carbohydrate, Fiber, Fat, Fatty Acids, Cholesterol, Protein and Amino Acids. Washington, DC: National Academic Press; pp. 1-19, 422-541, 769-879, 1228-1243 (2005).

Farrell PM et al. "Essential fatty acid deficiency in premature infants," Am J Clin Nutr. (2):220-229 (Aug. 48, 1988).

Gura et al. "Nutrition in Clinical Practice," 22: 664-672 (2007).

Gura KM et al. "Reversal of parenteral nutrition-associated liver disease in two infants with short bowel syndrome using parenteral fish oil: implications for future management," Pediatrics. 118(1):e197-201 (Jul. 2006).

Gura KM et al. "Safety and efficacy of a fish-oil-based fat emulsion in the reatment of parenteral nutrition-associated liver disease," Pediatrics. 121(3):e678-686 (Mar. 2008).

Holman R et al. "Essential fatty acid deficiency," Prog Chem Fats Other Lipids. 9:275-348 (1971).

Innis SM "Essential fatty acids in growth and development," Prog Lipid Res. 30(1):39-103 (1991).

Innis SM "Perinatal biochemistry and physiology of long-chain polyunsaturated fatty acids," J Pediatr. 143(4 Suppl): S1-8 (Oct. 2003).

Javid PJ et al. "The route of lipid administration affects parenteral nutrition-induced hepatic steatosis in a mouse model," J Pediatr Surg. 40(9):1446-1453 (Sep. 2005).

Jeppesen PB et al. "Essential fatty acid deficiency in patients receiving home parenteral nutrition," Am J Clin Nutr. 68 (1):126-133 (Jul. 1998).

Lee S et al. "Current clinical applications of omega-6 and omega-3 fatty acids," Nutr Clin Pract. 21(4):323-341 (Aug. 2006).

Marcus AD et al. "A Doctor's Push for Drug Pits Him Against Its Maker," The Wall Street Journal. A1, A15. (Nov. 13, 2006.).

Mohrhauer H et al. "The Effect of Dose Level of Essential Fatty Acids Upon Fatty Acid Composition of the Rat Liver," J Lipid Res. 4:151-159 (Apr. 1963).

Ryan AS et al. "Effect of DHA-containing formula on growth of preterm infants to 59 weeks postmenstrual age," Am J Human Biol. 11(4):457-467(1999).

Smit EN et al. "The possible role of essential fatty acids in the pathophysiology of malnutrition: a review. Prostaglandins Leukot Essent Fatty Acid," 71(4):241-250 (Oct. 2004).

Strijbosch RAM, et al. "Fish oil prevents essential fatty acid deficiency and enchances growth: clinical and biochemical implications," Metabolism Clinical and Experimental. 57:698-707(2008).

Waitzberg et al., Journal or Parenteral and Enteral Nutrition 30: 351-361(2006).

PDR—Ensure Light—p. 2338, 51st Edition (1997).

| TABLE 1: BASIC DIET (DYETS INC. AIN-93G PURIFIED RODENT DIET) | |
|---|---|
| INGREDIENTS | GRAMS/KILOGRAMS |
| CASEIN | 200 |
| CORNSTARCH | 397.486 |
| DEXTROSE | 132.00 |
| SUCROSE | 100.00 |
| CELLULOSE | 50.00 |
| t-BUTYLHYDROQUINONE | 0.014 |
| SALT MIX #210025 | 35.00 |
| VITAMIN MIX #310025 | 10.00 |
| L-CYSTINE | 3.00 |
| CHOLINE BITARTRATE | 2.5 |

*FIG. 6*

TABLE 2: RELEVANT PERCENTAGES OF FATTY ACID CONTENT BETWEEN MENHADEN AND SOYBEAN OIL.

| FAT COMPOSITION, % | MENHADEN OIL | SOYBEAN OIL |
|---|---|---|
| LINOLEIC | 1.5 | 54.8 |
| α-LINOLEIC | 1.6 | 7.8 |
| ARACHIDONIC ACID | 0.9 | - |
| EPA | 15.5 | - |
| DHA | 9.1 | - |
| OLEIC | 11.4 | 22.7 |
| PALMITIC | 17.1 | 10.2 |
| STEARIC | 2.8 | 4.5 |

*FIG. 7*

| Time points | Triglycerides in diets: | | | |
|---|---|---|---|---|
| | 1% | 5% | 10% | Soybean |
| Arachidonic acid (20:4) | | | | |
| Baseline | 0.2873 ± 0.0621 | 0.2140 ± 0.0092 | 0.2887 ± 0.0560 | 0.2651 ± 0.0474 |
| 3 weeks | 0.1876 ± 0.0221 | 0.1545 ± 0.0166 * | 0.0690 ± 0.0091 * | 0.2708 ± 0.0506 ‡, § |
| 6 weeks | 0.2196 ± 0.0249 * | 0.1115 ± 0.0243 * | 0.1449 ± 0.0146 * | 0.7150 ± 0.1533 †, ‡, § |
| 9 weeks | 0.1371 ± 0.0098 | 0.1254 ± 0.0052 | 0.0719 ± 0.0164 * | 0.2721 ± 0.1022 § |
| Mead acid (20:3n-9) | | | | |
| Baseline | 0.0024 ± 0.0024 | 0.0019 ± 0.0014 | 0.0056 ± 0.0043 | 0.0155 ± 0.0072 |
| 3 weeks | 0.0199 ± 0.0045 *, ‡, § | 0.0020 ± 0.0008 † | 0.0017 ± 0.0003 † | 0.0026 ± 0.0007 † |
| 6 weeks | 0.0210 ± 0.0039 *, ‡, § | 0.0020 ± 0.0018 † | 0.0015 ± 0.0008 † | 0.0000 ± 0.0000 † |
| 9 weeks | 0.0307 ± 0.0035 *, ‡, § | 0.0118 ± 0.0066 † | 0.0027 ± 0.0022 † | 0.0000 ± 0.0000 † |
| Eicosapentaenoic acid (20:5) | | | | |
| Baseline | 0.0747 ± 0.0200 | 0.0408 ± 0.0081 | 0.0735 ± 0.0124 | 0.0739 ± 0.0150 |
| 3 weeks | 0.2195 ± 0.0347 * | 0.4481 ± 0.0636 * | 0.2387 ± 0.0318 * | 0.0118 ± 0.0009 †, ‡, § |
| 6 weeks | 0.3691 ± 0.0449 *, ‡ | 0.4365 ± 0.0615 *, †, § | 0.4509 ± 0.0417 *, ‡ | 0.0148 ± 0.0090 †, ‡, § |
| 9 weeks | 0.2470 ± 0.0228 *, ‡ | 0.3884 ± 0.0269 *, †, § | 0.1984 ± 0.0428 *, ‡ | 0.0057 ± 0.0021 †, ‡, § |

*FIG. 8*

|  | Docosahexaenoic acid (22:6n-3) | | |
| --- | --- | --- | --- |
| Baseline | 0.1539 ± 0.0368 ‡ | 0.0735 ± 0.0304 *, †, § | 0.1534 ± 0.0169 ‡ |
| 3 weeks | 0.1351 ± 0.0156 *, ‡ | 0.2582 ± 0.0274 *, †, § | 0.0446 ± 0.0094 †, ‡, § |
| 6 weeks | 0.2281 ± 0.0246 *, ‡ | 0.2630 ± 0.0875 *, †, § | 0.1126 ± 0.0153 †, ‡, § |
| 9 weeks | 0.1474 ± 0.0117 * | 0.1872 ± 0.0073 * | 0.0372 ± 0.0099 †, ‡, § |
|  | Triene-tetraene ratio's | | |
| Baseline | 0.0050 ± 0.0050 | 0.0080 ± 0.0062 | 0.0594 ± 0.0260 |
| 3 weeks | 0.1049 ± 0.0204 *, ‡, § | 0.0135 ± 0.0062 * | 0.0095 ± 0.0017 † |
| 6 weeks | 0.0929 ± 0.0138 *, ‡, § | 0.0375 ± 0.0291 * | 0.0000 ± 0.0000 † |
| 9 weeks | 0.2269 ± 0.0253 *, ‡, § | 0.0894 ± 0.0497 *, † | 0.0000 ± 0.0000 †, ‡ |

(1) Values given are means +/- SE in nmol/ml. Only AA, Mead acid, EPA, DHA and triene-tetraene ratio's are shown.
(2) Diets are 1%, 5% and 10% menhaden oil diet and soybean diet.
* Value is significantly different from soybean oil group within same time point and acid (or ratio) group, $P < 0.05$.
† Value is significantly different from 1% menhaden oil group within same time point and acid (or ratio) group, $P < 0.05$.
‡ Value is significantly different from 5% menhaden oil group within same time point and acid (or ratio) group, $P < 0.05$.
§ Value is significantly different from 10% menhaden oil group within same time point and acid (or ratio) group, $P < 0.05$.

*FIG. 8 (cont'd)*

| Time points | Phospholipids in diets: | | | |
| --- | --- | --- | --- | --- |
| | 1% | 5% | 10% | Soybean |
| Arachidonic acid (20:4) | | | | |
| Baseline | 0.2535 ± 0.0122 | 0.2468 ± 0.0148 | 0.2507 ± 0.0312 | 0.2288 ± 0.0251 |
| 3 weeks | 0.2037 ± 0.0339 * | 0.1461 ± 0.0142 * | 0.1484 ± 0.0137 * | 0.8958 ± 0.0805 †, ‡, § |
| 6 weeks | 0.2378 ± 0.0041 * | 0.1334 ± 0.0182 * | 0.1574 ± 0.0044 * | 0.7139 ± 0.0316 †, ‡, § |
| 9 weeks | 0.1185 ± 0.0059 * | 0.1466 ± 0.0174 * | 0.1264 ± 0.0123 * | 0.9973 ± 0.0467 †, ‡, § |
| Mead acid (20:3n-9) | | | | |
| Baseline | 0.0000 ± 0.0000 | 0.0369 ± 0.0324 | 0.0029 ± 0.0029 | 0.0025 ± 0.0025 |
| 3 weeks | 0.0050 ± 0.0034 | 0.0062 ± 0.0059 | 0.0023 ± 0.0010 | 0.0003 ± 0.0003 |
| 6 weeks | 0.0192 ± 0.0060 *, ‡, § | 0.0046 ± 0.0028 † | 0.0005 ± 0.0004 † | 0.0031 ± 0.0014 † |
| 9 weeks | 0.0156 ± 0.0019 *, ‡, § | 0.0012 ± 0.0012 † | 0.0008 ± 0.0004 † | 0.0002 ± 0.0002 † |
| Eicosapentaenoic acid (20:5) | | | | |
| Baseline | 0.0489 ± 0.0106 | 0.0464 ± 0.0006 | 0.0597 ± 0.0026 | 0.0511 ± 0.0079 |
| 3 weeks | 0.2462 ± 0.0268 *, ‡ | 0.4152 + 0.0488 *, † | 0.4660 ± 0.0733 * | 0.0240 ± 0.0142 †, ‡, § |
| 6 weeks | 0.5370 ± 0.0273 *, ‡ | 0.3991 ± 0.0624 *, †, § | 0.5471 ± 0.0448 *, ‡ | 0.0265 ± 0.0025 †, ‡, § |
| 9 weeks | 0.2600 ± 0.0255 *, ‡ | 0.4353 ± 0.0459 *, †, § | 0.2779 ± 0.0313 *, ‡ | 0.0026 ± 0.0024 †, ‡, § |

*FIG. 9*

| | Docosahexaenoic acid (22:6n-3) | | |
|---|---|---|---|
| Baseline | 0.2504 ± 0.0421 | 0.2607 ± 0.0219 | 0.2990 ± 0.0300 | 0.2967 ± 0.0241 |
| 3 weeks | 0.4014 ± 0.0426 | 0.4522 ± 0.0574 | 0.3612 ± 0.0737 | 0.3576 ± 0.0357 |
| 6 weeks | 0.5006 ± 0.0277 * | 0.4694 ± 0.0717 | 0.3730 ± 0.0538 | 0.1767 ± 0.0325 † |
| 9 weeks | 0.5181 ± 0.0242 * | 0.3914 ± 0.0611 | 0.4034 ± 0.0226 | 0.3875 ± 0.0202 † |
| | Triene-tetraene ratio's | | |
| Baseline | 0.0000 ± 0.0000 | 0.0024 ± 0.0024 | 0.0079 ± 0.0079 | 0.0085 ± 0.0085 |
| 3 weeks | 0.0197 ± 0.0121 *, ‡, § | 0.0183 ± 0.0137 † | 0.0191 ± 0.0110 † | 0.0004 ± 0.0004 † |
| 6 weeks | 0.0810 ± 0.0252 *, ‡, § | 0.0327 ± 0.0200 † | 0.0030 ± 0.0027 † | 0.0044 ± 0.0021 † |
| 9 weeks | 0.1308 ± 0.0139 *, ‡, § | 0.0066 ± 0.0066 † | 0.0062 ± 0.0028 † | 0.0002 ± 0.0002 † |

(1) Values given are means +/- SE in nmol/ml. Only AA, Mead acid, EPA, DHA and triene-tetraene ratio's are shown.
(2) Diets are 1%, 5% and 10% menhaden oil diet and soybean oil diet.
* Value is significantly different from soybean oil group within same time point and acid (or ratio) group, $P < 0.05$.
† Value is significantly different from 1% menhaden oil group within same time point and acid (or ratio) group, $P < 0.05$.
‡ Value is significantly different from 5% menhaden oil group within same time point and acid (or ratio) group, $P < 0.05$.
§ Value is significantly different from 10% menhaden oil group within same time point and acid (or ratio) group, $P < 0.05$.

*FIG. 9 (cont'd)*

| DIET | PAIR FED | AD LIBITUM |
|---|---|---|
| 1% | 144.34±1.99 | 132.81±2.43 |
| 5% | 160.95±4.16 | 160.36±10.38 |
| 10% | 190.50±14.02 | 194.58±1.80 |
| SOYBEAN | 142.07±0.94 | 152.32±3.95 |

*FIG. 10A*

| COMPARISON FOR FACTOR: | DIFF OF MEANS | UNADJUSTED P | SIGNIFICANT? |
|---|---|---|---|
| PAIR FED VS. AD LIB | 1.311 | 0.800 | NO |
| DIETS WITHIN PAIR FED GROUPS | | | |
| 10% VS. 1% | 46.162 | <0.001 | YES |
| 10% VS. SOYBEAN | 40.980 | <0.001 | YES |
| 10% VS. 5% | 29.555 | 0.006 | YES |
| 5% VS. 1% | 16.607 | 0.110 | NO |
| 5% VS. SOYBEAN | 11.425 | 0.267 | NO |
| SOYBEAN VS. 1% | 5.182 | 0.612 | NO |
| DIETS WITHIN AD LIBITUM GROUPS | | | |
| 10% VS. 1% | 61.771 | <0.001 | YES |
| 10% VS. SOYBEAN | 42.256 | <0.001 | YES |
| 10% VS. 5% | 34.214 | 0.003 | YES |
| 5% VS. 1% | 27.557 | 0.015 | YES |
| SOYBEAN VS. 1% | 19.515 | 0.063 | NO |
| 5% VS. SOYBEAN | 8.042 | 0.751 | NO |

(1) GROUPS ARE DIETS WITH 1%, 5% AND 10% MENHADEN OIL AND SOYBEAN OIL, PAIR FED AND AD LIBITUM.

*FIG. 10B*

| % OF TOTAL ENERGY | LINOLEIC ACID | ARACHIDONIC ACID | TOTAL OMEGA-6 |
|---|---|---|---|
| 1% MENHADEN OIL | 0.0393 | 0.0236 | 0.0629 |
| 5% MENHADEN OIL | 0.196 | 0.118 | 0.314 |
| 10% MENHADEN OIL | 0.393 | 0.236 | 0.629 |
| SOYBEAN OIL | 6.7 | - | 6.7 |

(1) STANDARD REQUIREMENT BELIEFS ARE 1% FOR OMEGA-6 FATTY ACIDS.

*FIG. 11*

DIETARY FORMULATIONS AND METHODS FOR TREATMENT OF INFLAMMATION AND OTHER DISORDERS

RELATED APPLICATIONS

This application is a continuation of U.S. patent application Ser. No. 12/602,054, filed Nov. 25, 2009, which is a 371 of PCT/US2008/006691, filed May 27 2008, now issued as U.S. Pat. No. 8,652,508, which claims a benefit of the U.S. Provisional Application 60/931,888, filed May 25, 2007. The contents of these applications are incorporated by reference in their entirety into the instant application.

FIELD OF THE INVENTION

The present application relates to the field of dietary supplement and to formulations for total enteral or parenteral nutrition and the prevention of fatty acid deficiency.

BACKGROUND OF THE INVENTION

Linoleic acid and alpha-linolenic acid are two fatty acids that cannot be synthesized by humans, thus these two fatty acids are considered to be Essential Fatty Acids (EFA's) necessary in human nutrition. Linoleic acid and alpha-linolenic acid form polyunsaturated fatty acids of the omega-6 series and omega-3 series, respectively, through enzymatic desaturation and elongation principally by the liver. While man and other mammals can desaturate or elongate the fatty acid chains they cannot interconvert the fatty acids from one family to another (e.g. Omega-6 to Omega-3). Accordingly, both linoleic and alpha-linoleic fatty acids have been included in all total Enteral and Parenteral Nutritional products to date.

In the United States it is recommended that 3% of the total calories in the diet be from linoleic acid. Linoleic acid intake at levels from 1% to 2% of total dietary calories is believed to be sufficient to prevent both biochemical and clinical evidence of deficiency in several animal species and humans. The Academy of Pediatrics has recommended that infant formulas provide at least 2.7% of energy as linoleic acid (Recommended Dietary Allowances 10$^{th}$ Edition, 1989, Author: Subcommittee on the Tenth Edition of the RDA's Food and Nutrition Board Commission on Life Sciences; Publisher: National Academy Press Washington, D.C.)

Essential fatty acids are known to play a part in many metabolic processes, and there is evidence to suggest that low levels of essential fatty acids, or the wrong balance of types among the essential fatty acids, may be a factor in a number of illnesses including, for example, metabolic syndrome, heart disease, fatty liver disease, obesity and diabetes.

Accordingly, it is important to have an improved understanding of the essential fatty acids and their effects so that better nutritional programs can be designed.

Parenteral nutrition (PN) is a life-saving therapy for patients unable to absorb enteral nutrients secondary to insufficient intestinal length or function. Before the development of PN, patients with insufficient gastrointestinal absorptive function commonly died of starvation and subsequent complications of malnutrition[1]. Today, more than 30,000 patients in the US are permanently dependent on PN for survival. Long-term use of PN, however, is associated with many complications, including blood stream infections, metabolic abnormalities and organ dysfunction[2]. The most serious complication in children continues to be PN-associated liver disease (PNALD), whose etiology has been demonstrated by our team to be at least in part due to the lipid emulsion component[3,4]. The most effective treatment for PNALD is increasing enteral energy intake while reducing PN, but this process is often impossible when intestinal function is poor[5,6]. In some cases of liver dysfunction in the setting of intestinal failure, liver-small intestine transplantation remains the only treatment option. Infants with PNALD have a mortality rate approaching 100% within a year of diagnosis if they are unable to be weaned off PN or fail to receive a liver/small bowel transplant[7]. Recent evidence suggests that PNALD may be in part due to the lipid component that is rich in soy oils containing large quantities of pro-inflammatory omega-6 fatty acids and hepatotoxic phytosterols [8,9]. A fish oil-based lipid emulsion has been shown to be hepatoprotective in mice and efficacious in the treatment of PNALD in children[3, 4, 10, 11].

SUMMARY OF THE INVENTION

Embodiments of the present invention are based on the observation that, contrary to current understanding, linoleic acid is not actually a true essential fatty acid. Thus, linoleic acid need not be incorporated in enteral or parenteral nutritional products that provide complete nutrition. Furthermore, in accordance with the present invention it has been determined that only minimal levels of a downstream product of linoleic acid, arachidonic acid, are important for good nutrition and prevention of essential fatty acid deficiency. As arachidonic acid is a pro-inflammatory substance, these minimal levels reduce overall inflammation in a subject. Furthermore, having reduced to no linoleic acid in a nutritional product will lower arachidonic acid levels without producing essential fatty acid deficiency and inflammation and improve immune response to infection.

Accordingly, in one embodiment, the invention provides a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation.

In one embodiment, the dietary formulation comprises 0.15% to 0.30% by calories of arachidonic acid, or 0.15% to 0.6% by calories of archidonic acid.

In one embodiment, the $C_{20}$ or longer omega-3 fatty acid consists of eicosapentaenoic acid (EPA), or docosahexaenoic acid (DHA), or eicosatetraenoic acid, or 5-docosapentaenoic acid, or combinations thereof; and comprises about 0% by calories of omega-6 fatty acids other than arachidonic acid, about 0% by calories of linoleic acid, and about 0% by calories of alpha-linolenic acid. Preferably, the ratio of $C_{20}$ or longer omega-3 fatty acid to arachidonic acid is from about 10:1 to about 40:1. For example, the ratio is about 10:1, about 20:1, about 30:1, or about 40:1.

In one embodiment, the arachidonic acid is provided as dihomo-gamma-linolenic acid or gamma-linolenic acid which is converted in vivo to arachidonic acid, wherein the dihomo-gamma-linolenic acid or gamma-linolenic acid is provided in amounts of 0.45% to 6.0% by calorie.

In one embodiment, the $C_{20}$ or longer omega-3 fatty acid is selected from the group consisting of eicosapentaenoic acid (EPA), docosahexaenoic acid (DHA), an octadecatetraenoic acid, an eicosatetraenoic acid, and mixtures thereof.

Another aspect of the present invention relates to a dietary formulation for total enteral or parenteral nutrition, or a dietary supplement, that provides restricted omega-3 and omega-6 fatty acid delivery to an individual, wherein the omega-3 and omega-6 fatty acid is one or more $C_{20}$ or longer omega-3 fatty acids, and arachidonic acid.

In one embodiment, the $C_{20}$ or longer omega-3 fatty acid is eicosapentaenoic acid (EPA), docosahexaenoic acid (DHA), or 5-docosapentaenoic acid, or combinations thereof.

In one embodiment, the ratio of omega-3 fatty acid to arachdonic acid is from about 10; 1 to about 40:1. For example, the ratio is about 10:1, about 20:1, about 30:1, or about 40:1. In one embodiment, the arachidonic acid is equal to or less than about 2.7 kilocalories/kg body weight for an adult, or 9 kilocalories/kg body weight for an infant or child.

In one embodiment, the dietary formulation or supplement further comprises additional components such as one or more omega-9 fatty acids (e.g. linoleic acid), a source of carbohydrate, a source of protein, a source of vitamins and minerals, an emulsifier.

In one embodiment, the arachidonic acid and the omega-3 fatty acid are provided by fish, or fungal oil, or from genetically altered plants that produce arachidonic acid or immediate precursors of arachidonic acid, e.g. gamma linolenic and dihomogammalinolenic acid.

In one embodiment, the dietary formulation further comprises a source of carbohydrate. The source of carbohydrates can be any simple or complex carbohydrate, e.g., monosaccharides, disaccharides, or oligosaccharides. In one embodiment the source of carbohydrate is corn starch, dextrose and glucose, corn starch, dextrose and glucose.

In one embodiment, the dietary formulation further comprises a source of protein. The source of protein can be any protein hydrolysate or peptide mixtures, amino acid mixtures of high biologic values, e.g., meat, milk, egg or soy proteins. The protein hydrolysate can be partially hydrolyzed in nature and include a substantial fraction of variable chain length peptides, e.g., medium or short chain peptides, e.g., di- and tri-peptides, but have less than about 10% free amino acids, more preferably less than about 5% free amino acids. In one embodiment, only the highest biological value proteins are hydrolyzed, e.g., whey, lactalbumin, casein, egg white, egg solids, soy, or delactosed milk solids. In other embodiments, the protein source is lactose-free, and free amino acids are preferably avoided in the formulation of the invention.

In one embodiment, the dietary formulations further comprise a source of vitamins and minerals. For example, vitamins and minerals in accordance with, or approximately, the Recommended Dietary Allowance (RDA), now called the Daily Reference Intake (DRI). The dietary formulations can also contain nutrients not recommended by the RDA, e.g., nucleotides, beta-carotene, carnitine, and taurine.

In one embodiment, the dietary formulation further comprises an emulsifier or other inactive ingredients such as artificial sweeteners and/or flavoring.

The dietary formulations of the present invention may be in the form of a dietary supplement (food oil) or used as a total enteral or parenteral feeding regimen. In one embodiment, the dietary formulation is a total parenteral formulation. In another embodiment, the formulation is an total enteral formulation for tube feeding or oral administration. In still another embodiment, the dietary formulation is food oil provided in a form suitable for oral administration. When the dietary formulation is for total enteral or parenteral feeding, the formulation should contain all essential amino acids, as well as essential vitamins and minerals to ensure that the patient is obtaining all necessary nutrients. When the formulation is in the form of a dietary supplement (food oil), the formulation should provide about 5-60% of total energy expenditure in terms of calories.

In another aspect of the invention, a method of treating essential fatty acid deficiency in a subject is provided that comprises administering to the subject the dietary formulation of the invention, where the formulation is in the form of an oil emulsion providing total enteral or parenteral nutrition, or in the form of food oil suitable for oral administration, and comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1.0% by calorie, 0.15% to 3.0% by calorie, or in amounts of 0.45% to 6.0% by calorie, as there is not 100% conversion of dihomo-gamma-linolenic acid or gamma-linolenic acid to arachidonic acid. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In still another aspect of the invention, a method of treating/preventing an inflammatory disease or disorder in a subject is provided that comprises administering to the subject a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In one embodiment, the inflammatory disease or disorder is selected from the group consisting of diabetes-associated nephropathy and retinopathy, protein wasting, muscle fatigue or inflammation, coronary artery disease, inflammatory bowel disease, atherosclerosis, Alzheimer's disease, myocarditis, cardiomyopathy, acute endocarditis, pericarditis, hepatitis, Systemic Inflammatory Response Syndrome (SIRS)/sepsis, adult respiratory distress syndrome (ARDS), asthma, rheumatoid arthritis, osteoarthritis, systemic lupus erythematosis, airway hyperresponsiveness (AHR), bronchial hyperreactivity, chronic obstructive pulmonary disease (COPD), congestive heart failure (CHF), inflammatory complications of diabetes mellitus, metabolic syndrome, non-alcoholic fatty liver disease, end stage renal disease (ESRD), and dermatitis.

In another embodiment, a method of treating malnutrition accompanying cancer in a subject is provided that comprises administering to a subject the dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1.0% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In one embodiment, the subject treated has pancreatic cancer, stomach cancer, colon cancer, esophageal cancer, lung cancer (e.g. small cell cancer), brain cancer, ovarian cancer, leukemia, lymphoma, or any other cancer that is accompanied by a high likelihood of malnutrition (cancer cachexia), e.g. any cancer related to the digestive system or any other cancer complicated by malnutrition which includes non-digestive system cancers.

In another aspect of the invention, a method of increasing the immunity of a subject is provided that comprises administering to a subject a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1.0% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In still another aspect, a method of minimizing a risk of infection in a subject is provided that comprises administering to said subject a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In one embodiment the subjects to be treated are critically ill. The subject can be critically ill for a variety of reasons including surgery, burns, trauma, cancer (e.g., pancreatic cancer, colon cancer, stomach cancer, esophageal cancer, lung cancer, ovarian cancer, brain cancer, leukemias and lymphoma), AIDS, multisystem organ failure, sepsis or inflammatory process which can impair fatty acid elongation and desaturation. It is also useful for individuals who may have an infection at the time of the administration of the dietary formulation or may be at high risk of infection due to some sort of immunocompromise. Individuals at risk of infection include those suffering with secondary immunosuppression due to chemotherapy or diabetes mellitus, protein-malnourished patients, or patients undergoing surgery, e.g., abdominal or thoracic surgery.

In another aspect of the invention, a method of treating a liver transplant donor is provided. The method comprises administering a dietary formulation in the form of an oil emulsion providing total enteral or parenteral nutrition, or in the form of food oil suitable for oral administration, to the donor prior to donation of the liver, wherein the donor is treated for a period of time sufficient to reduce the fat content of the liver. The dietary formulation can given orally or enterally for four to six weeks, or intravenously for four to five days prior to liver donation. The dietary formulation comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In another aspect of the invention, a method of treating a subject prior to a surgical procedure in said subject is provided. The method comprises comprising administering the dietary formulation said subject a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. In one embodiment, the dietary formulation is given orally or enterally for four to six weeks, or intravenously for four to five days prior to surgery. The dietary formulation may comprise 0.15% to 0.30% by calories arachidonic acid, or 0.15% to 0.6% by calories of archidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In still another aspect of the invention, a method of preventing excessive weight gain in a subject with insulin resistance is provided. The method comprises administering to said subject a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of arachidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1.0% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In still another aspect of the invention, a method of treating obesity in a subject is provided. The method comprises administering said subject administering to said subject a dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of archidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In yet another aspect of the invention, a method of reducing the level of an inflammatory biomarker in a subject that correlates to an inflammatory condition is provided. The method comprises, administering to the subject a dietary formulation, wherein the formulation is administered in an amount sufficient to reduce the level the inflammatory biomarker. The dietary formulation is in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and wherein said fatty acids provide 5-60% of the total calories of said dietary formulation. The dietary formulation may comprise 0.15% to 0.30% by calories arachidonic acid, or 0.15% to 0.6% by calories of archidonic acid. The arachidonic acid can be provided as dihomo-gamma-linolenic acid or gamma-linolenic acid which is converted in vivo to arachidonic acid, wherein the dihomo-gamma-linolenic acid or gamma-linolenic acid is provided in amounts of about 0.15%-1% by calorie, 0.15% to 3.0% by calorie, or in amounts of 0.45% to 6.0% by calorie. The $C_{20}$ or longer omega-3 fatty acid can be eicosapentaenoic acid (EPA), docosahexaenoic acid (DHA), an octadecatetraenoic acid, an eicosatetraenoic acid, or mixtures thereof. In one embodiment, the arachidonic acid and the omega-3 fatty acid are provided by fish or fungal oil. The dietary formulation can further comprise a source of carbohydrate, a source of protein, a source of vitamins and minerals, and/or an emulsifier or other inactive ingredients such as artificial sweeteners and/or flavoring.

In one embodiment, the inflammatory biomarker is selected from the group consisting of C-reactive protein (CRP), interleukin-1-alpha (IL-1-alpha), interleukin-1-beta (IL-1-beta), interleukin-6 (IL-6), soluble TNF receptors I and II, oxidative metabolites of protein, carbohydrate, fat, DNA, and elevated white blood cell count (WBC).

In another embodiment of the invention, the dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and said fatty acids provide 5-60% of the total calories of said dietary formulation, and wherein said formulation comprises about 0.9%, or 0.8%, or 0.7%, or 0.6%, or 0.5%, or 0.4%, or 0.3%, or 0.2%, or 0.1%, or 0% by calories of omega-6 fatty acids.

In still another embodiment, the dietary formulation, the dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and said fatty acids provide 5-60% of the total calories, and wherein said dietary formulation comprises about 0.9%, or 0.8%, or 0.7%, or 0.6%, or 0.5%, or 0.4%, or 0.3%, or 0.2%, or 0.1%, or 0% by calories of linoleic acid.

In yet another embodiment, the dietary formulation in the form of an oil emulsion providing total enteral or parenteral nutrition, or in the form of food oil suitable for oral administration, that comprises about 2-60% by calories of a $C_{20}$ or longer omega-3 fatty acid; and about 0.05% to 1% by calories of arachidonic acid, where the formulation provides less than 1% of total calories from linoleic acid and alpha-linolenic acid, and said fatty acids provide 5-60% of the total calories of said dietary formulation comprises, and wherein said dietary formulation comprises about 0.9%, or 0.8%, or 0.7%, or 0.6%, or 0.5%, or 0.4%, or 0.3%, or 0.2%, or 0.1%, or 0% by calories of alpha-linolenic acid.

BRIEF DESCRIPTION OF THE DRAWINGS

FIG. 6 is a table (Table 1) illustrating the ingredients of the basic diet of the animals.

FIG. 7 is a table (Table 2) which indicates the relevant percentages of fatty acid content between menhaden and soybean oil.

FIG. 8 is a table (Table 3a) which indicates fatty acid concentration in nmol/ml of relevant plasma triglycerides at baseline, 3, 6 and 9 week time points for pair fed groups (n=5) on different diets. Diets are 1%, 5%, and 10% menhaden oil diets and soybean diet.

FIG. 9 is a table (Table 3b) which indicates fatty acid concentration in nmol/ml of relevant plasma phospholipids at baseline, 3, 6 and 9 week time points for pair fed groups (n=5) on different diets. Diets are 1%, 5%, and 10% menhaden oil diets and soybean diet.

FIGS. 10A and 10B are tables (Table 4A and Table 4B respectively). Table 4a shows the average (n=5) sums of double bonds with standard errors for diets in pair fed and ad libitum groups. Table 4B shows a two-way analysis of variance for number of double bonds between diets, for pair fed and ad libitum groups. Diets are 1%, 5%, and 10% menhaden oil diets and soybean diet.

FIG. 11 is a table (Table 5) which indicates the percentages of energy provided by LA, AA, and total omega-6 fatty acids for the menhaden and soybean oil diets.

DETAILED DESCRIPTION OF THE INVENTION

Figure 1:
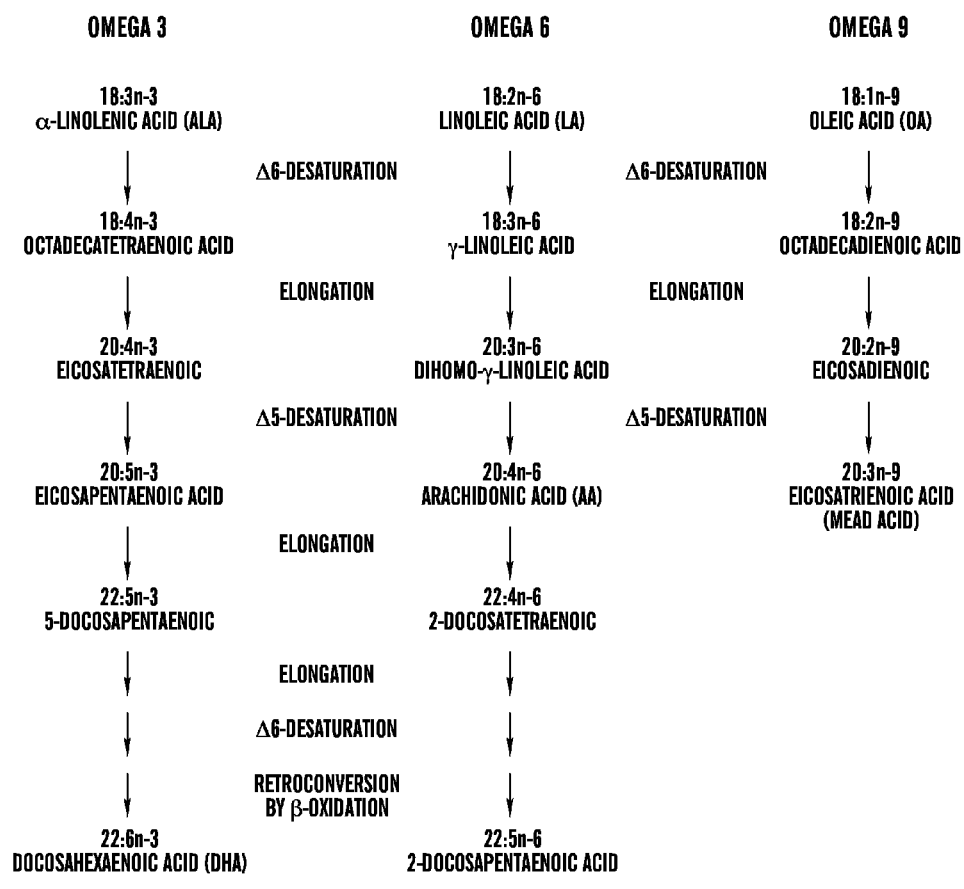
FIG. 1 is a diagrammatic illustration of the metabolic pathways in fatty acid synthesis.

Aspects of the present invention relate to the finding that mammals do not need as much omega-6 (e.g. arachidonic acid) in their diets as previously believed. Aspects of the present invention are also related to the finding that mammals do not need much if any linoleic acid and alpha-linoleic acid, as long as they have alternative sources of arachidonic acid and C-20 or longer omega-3 fatty acids that are sufficient to meet the minimal dietary requirements described herein. Since the omega-6 biosynthetic pathway leads to pro-inflammatory mediators, having an overabundance of such omega-6 fatty acids (e.g., arachidonic acid) can lead to unnecessary inflammation. Conversely, having the minimum necessary levels present in the body serves to minimize inflammation. In addition, omega-3 fatty acids have anti-inflammatory effects. So, having a healthy abundance of omega-3 fatty acids will further serve to reduce unwanted inflammatory effects. Presently, it is believed that linoleic acid intake from 1% to 2% of the total dietary calories is necessary to prevent fatty acid deficiency, and it is recommended that linoleic acid provide 3% of total dietary calories.

Applicants have discovered that considerably less linoleic acid and/or alpha-linoleic acid intake will produce the same beneficial dietary results, while also having a significant advantageous effect on the recipient by eliminating liver damage and reducing inflammation. Applicants have further discovered that if sufficient amounts of arachidonic acid are provided in the diet, subjects require no dietary linoleic acid. Further, these necessary and sufficient amounts of arachidonic acid are considerably less than previously realized. Dietary formulations and dietary supplements that contain the reduced amounts of fatty acids indicated from these findings can be safely administered to subjects without risk of fatty acid deficiency. Such administration will minimize liver damage that has previously resulted from higher omega-6 diets, and can further be used to reduce unwanted inflammatory responses in an individual.

Dietary formulations are provided that include minimal levels of arachidonic acid. The formulations described herein are to be used for total enteral or parenteral nutrition. Alternatively, dietary supplements (food oil) suitable for oral administration are provided that are used to deliver to a recipient subject the same amount of the various omega-3 and omega-6 fatty acids, in combination with their own diet. The dietary formulations for total enteral or parenteral nutrition described herein contain about 2-60% by calories of a $C_{20}$ or longer omega-3 fatty acid and about 0.05% to 1% by calories of arachidonic acid. The dietary formulation will also further comprise alternate caloric sources sufficient to produce 100% of the calories administered to the recipient subject (e.g., 40% calories from alternate sources when the formulation provides 60% calories from the specified fatty acids). The formulation, as generated for total nutrition provides less than 1% of total calories from linoleic acid and alpha-linolenic acid, and the fatty acids provide 5-60% of the total calories of the dietary formulation. In one embodiment, the formulation includes about 0.3% to 0.15% by calories arachidonic acid.

Dietary supplements likewise can be formulated from the findings described herein. The term dietary supplement is generally used to refer to a composition which a subject ingests to augment or supplement their diet. The diet that is supplemented may be the usual diet the subject ingests, or may be a specifically formulated diet designed to complement the formulation in producing the desired levels of omega-3 and omega-6 fatty acids in the subject's body. In one embodiment, the dietary supplement provides all of the omega-3 and omega-6 fatty acids in the recipient subject's diet. Such a supplement preferably includes about 2-60% by calories of a $C_{20}$ or longer omega-3 fatty acid and about 0.05% to 1% by calories of arachidonic acid. The supplement provides less than 1% of total calories from linoleic acid and alpha-linolenic acid, and the fatty acids provide 5-60% of the total calories of the supplement. In one embodiment, the supplement includes about 0.3% to 0.15% by calories arachidonic acid. In such embodiments, the dietary supplement may contain additional caloric components such as those described herein. However, the supplement need not necessarily contain all calories supplied to a subject. As such, it may contain higher percentage by total calorie of the $C_{20}$ or longer omega-3 fatty acid, arachidonic acid, linoleic acid, and alpha linoleic acid. Preferably, however, the dietary supplement, when combined with the subjects diet, provides the same relative amounts of these components as are present in the total nutrition dietary formulations described herein. More preferably, the subject's diet which is supplemented contains reduced to no omega-6 fatty acids and omega-3 fatty acids, to ultimately provide overall intake in the subject comparable to that which is produced by administration of the dietary formulations for total enteral or parenteral nutrition described herein.

Linoleic acid is an unsaturated omega-6 fatty acid that is converted to arachidonic acid in the body. It is abundant in many vegetable oils, especially safflower and sunflower oils. Importantly, the amount of linoleic acid is limited in the dietary formulation and supplements of the invention. In one embodiment, the dietary formulation or supplement provides only about 0.9%, or 0.8%, or 0.7%, or 0.6%, or 0.5%, or 0.4%, or 0.3%, or 0.2%, or 0.1%, or 0% by calories of linoleic acid (omega-6 fatty acid). In one embodiment, the dietary formulation or supplement provides 0.075% linoleic acid by calories. In another embodiment, the formulation or supplement includes less than about 0.5% by calories combined linoleic acid and alpha-linoleic acid. In another embodiment, the dietary formulation or supplement provides from 0% to 0.1% linoleic acid by calories such that the total diet contains 0% to 0.1% linoleic acid. And in such a formulation, optionally alpha linoleic acid is not present or is present only in trace amounts. The alpha linoleic acid content can be very low to nothing in diets where there is sufficient omega-3 provided (e.g., as EPA or DHA, or other 20 carbon fatty acids).

In one embodiment, the dietary formulation or supplement is made from an oil in which 1.5% of the calories are linoleic acid, to produce a dietary formulation with 0.075% calories linoleic acid.

Alpha-linoleic acid is an unsaturated omega-3 fatty acid that is converted to either DHA or EPA in the body. It is abundant in many seed oils, notably rapeseed (canola), soybeans, walnuts, flaxseed (Linseed), perilla, chia and hemp. ALA is also obtained from the thylakoid membranes of the green leaves of broadleaf plants (the membranes responsible for photosynthesis). Greens, therefore, and animals that eat greens, are often a good source of ALA. Importantly, the amount of alpha linoleic acid is also limited in the dietary formulation and supplements of the invention. In one embodiment, the dietary formulation or supplement includes only about 0.9%, or 0.8%, or 0.7%, or 0.6%, or 0.5%, or 0.4%, or 0.3%, or 0.2%, or 0.1%, or 0% by calories of alpha linoleic acid.

Arachidonic acid is a polyunsaturated omega-6 fatty acid that is present in the phospholipids (especially phosphatidylethanolamine, phosphatidylcholine and phosphatidylinositides) of membranes of the body's cells, and is abundant in the brain. It is also involved in cellular signaling as a second messenger. It is also the precursor of eicosanoids, a family of other molecules with specific important roles in the body. It can be generated in the body from linoleic acid. In one embodiment, the dietary formulation or supplement includes only about 0.15% to 0.6% by calories arachidonic acid. Preferably the total diet should provide less than 0.6% by calories arachdonic acid. In another embodiment, the dietary formulation or supplement includes only about 0.1% by calories of arachidonic acid.

In one embodiment, the dietary formulation or supplement comprises about 0.9%, 0.8%, 0.7%, 0.6%, 0.5%, 0.4%, 0.3%, 0.2%, 0.1%, or 0% by calories of omega-6 fatty acids other than the arachidonic acid. In a preferred embodiment, the formulation or supplement contains no additional omega-6 fatty acids, other than arachidonic acid. Preferred ratios of omega-3 fatty acid, to arachidonic acid fall within the range of about 10:1 to 40:1. In one embodiment, the ratio is 10:1, 20:1, 30:1, or 40:1. Preferred omega-3 fatty acids are DHA, EPA, and combinations thereof.

Another aspect of the invention relates to a dietary formulation for total enteral or parenteral nutrition, or a dietary supplement, that provides restricted omega-3 and omega-6 fatty acid delivery to an individual, wherein the omega-3 fatty acid is a $C_{20}$ or longer omega-3 fatty acid, and wherein the omega-6 fatty acid is arachidonic acid. Dietary formulations that are formulated for total nutrition of the recipient will contain additional components required for the total nutrition of the recipient, who is to receive no other source of nutrition. Nonlimiting examples of such additional components are described herein, and can otherwise be readily determined by the skilled practitioner.

In one embodiment, the dietary formulation for total enteral or parenteral nutrition, or dietary supplement, provides the $C_{20}$ or longer omega-3 fatty acid as eicosapentaenoic acid (EPA), docosahexaenoic acid (DHA), 5-docosapentaenoic acid, or combinations thereof. In one embodiment DHA alone is used. In another embodiment, EPA alone is used. Alternatively, combinations of EPA and DHA are used, and such combinations are expected to produce comparable results as DHA alone. The exact amounts of arachidonic acid and the omega-3 fatty acid in the formulation or supplement are based on total desired caloric intake and desired caloric % of the omega-3 and omega-6 fatty acids for the recipient individual. Preferably, the omega-3 fatty acid to arachidonic acid ratio of the formulation or supplement is from about 10:1 to about 40:1 (e.g., about 10:1, 20:1, 30:1, or 40:1). The formulation or supplement may optionally further comprise one or more additional components which do not directly influence the omega-3 or omega-6 levels of the recipient (e.g., omega-9 fatty acids, a source of carbohydrate, a source of protein, a source of vitamins and minerals, an emulsifier, and combinations thereof). It may optionally provide linoleic acid and/or alpha linoleic acid in amounts up to 0.1% total calories of linoleic acid or linoleic+alpha linoleic acid.

In one embodiment, the dietary formulation or supplement provides the minimal amount of arachidonic acid necessary and sufficient to fulfill the membrane requirements of the recipient individual. Such low levels of arachidonic acid will promote a potent anti-inflammatory environment. This is accomplished by maintaining enough arachidonic acid to keep the triene/tetraene ratio <2. In order to accomplish this preferred ratio, the formulation or diet can also be manipulated to lower levels of the triene mead acid.

A composition for producing the dietary formulation for total enteral or parenteral nutrition consisting essentially of the fatty acid component is further envisioned in the invention. Such a composition will generally take the form of an oil (or an oil emulsion) and contain the specified $C_{20}$ or longer omega-3 fatty acid and arachidonic acid in the specified amounts. Preferably, the omega-3 fatty acid to arachidonic acid ratio of the oil composition is from about 10:1 to about 40:1 (e.g., about 10:1, 20:1, 30:1, or 40:1).

One of skill in the art will recognize that the specified recommended amounts of arachidonic acid for the recipient individual can optionally be provided by instead providing a precursor which is converted to arachidonic acid in vivo upon ingestion. As such, another embodiment of the invention is a formulation or supplement that comprises dihomo-gamma-linolenic acid and/or gamma-linolenic acid (which is converted in vivo to arachidonic acid) wherein the dihomo-gamma-linolenic acid or gamma-linolenic acid in amounts to generate the desired arachidonic acid in the subject. In one embodiment, the dihomo-gamma-linolenic acid and/or gamma-linolenic acid is provided in amounts of about 0.15% to 1.0% by calorie, about 0.15% to 3.0%, about 0.45% to 0.3% by calorie, or 0.45% to 6.0% by calorie. The dihomo-gamma-linolenic acid and/or gamma-linolenic acid are present either in combination with arachidonic acid or in the absence of arachdonic acid, in the appropriate respective amounts. Such amounts can be readily determined by the skilled practitioner.

When appropriately administered to an individual, the dietary formulations and dietary supplements of the present invention are especially useful in reducing or maintaining reduced levels of inflammatory fatty acids in the body of the recipient subject. In one embodiment, the dietary formulation or supplement provides the desired level of restricted omega-3 and omega-6 fatty acid to a subject by having as it contents $C_{20}$ or longer omega-3 fatty acid as the only omega-3 in the formulation or supplement, and by having as its contents arachidonic acid as the only omega-6 source in the formulation or supplement. In one embodiment, the dietary formulation or supplement is used as the only source of fatty acids for the recipient subject.

One important function of the dietary formulation and supplements described herein is to provide for restricted omega-3 and omega-6 fatty acid delivery to an individual. As such, the term "consisting essentially of" or "consists essentially of" as used herein to describe the contents of a formulation or supplement, refers to the absence of other, non-specified ingredients that either are omega-3 or omega-6 fatty acids, and/or can be metabolized into omega-3 and/or omega-6 fatty acids (e.g., linoleic acid, alpha-linoleic acid, dihomo-gamma-linoleic acid, and gamma-linoleic acid). It also refers to the presence in merely trace amounts, of such other ingredients that are, or can be, metabolized into omega-3 and/or omega-6 fatty acids. It however allows for the presence of other useful ingredients which will not significantly effect the omega-3 or omega-6 fatty acid levels of the recipient subject. As such, in one embodiment, the dietary formulations and supplements described herein consist essentially of the listed omega-3 and omega-6 fatty acid components.

The dietary formulations of the invention can be made by blending the fat fraction, containing at least the $C_{20}$ or longer omega-3 fatty acid moiety and the arachidonic acid moiety, with any proteins, carbohydrates, and/or other additional additives, and homogenizing the mixture into a stable emulsion.

Sources for the omega-3 fatty acids are plant oils, marine plankton, fungal oils, and fish oils. Suitable fish oils include, but are not limited to cod, menhaden, herring, mackerel, caplin, tilapia, tuna, sardine, pacific saury, krill, salmon, and the like. Fish oil is available commercially, for example 10% (wt/wt) fish oil triglycerides can be obtained from Nisshin Flour Milling Co. located in Nisshin, Japan. Arachidonic acid is commercially available from Martek, Inc. as a fungal derivative which contains 50% arachidonic acid.

The dietary formulations of the present invention may be used for a total enteral or parenteral feeding regimen. In one embodiment, the dietary formulation is a total parenteral formulation. In another embodiment, the formulation is a total enteral formulation for tube feeding or oral administration. In still another embodiment, the dietary formulation is food oil provided in a form suitable for oral administration. When the dietary formulation is for total enteral or parenteral feeding, the formulation will preferably contain all essential amino acids, as well as essential vitamins and minerals to ensure that the patient is obtaining all necessary nutrients. When the compositions described herein are in the form of a dietary supplement (food oil), the composition can provide about 5-60% of total energy expenditure in terms of calories (e.g. 5%, 10%, 20%, 30%, 40%, 50%, or 60%).

The formulations described herein may also take the form of a dietary supplement (food oil), suitable for oral administration. Use of such a supplement is expected to produce the same beneficial results as described herein for the dietary formulations for total enterla or parenteral nutrition, when combined with a diet which appropriately limits fatty acid intake.

In one embodiment, the dietary formulation or supplement includes a protein hydrolysate. The protein hydrolysate may be any suitable partially hydrolyzed protein or protein hydrolysate utilized in a nutritional formula such as soy protein hydrolysate, casein hydrolysate, whey protein hydrolysate, animal and vegetable protein hydrolysates, partially hydrolyzed whey, casein or soy proteins, and mixtures thereof. Soy or casein protein hydrolysates comprising a substantial proportion of variable chain length peptides, e.g., medium chain and short chain peptides, e.g., di- and tri-peptides, but having less than about 10% free amino acids, possibly less than about 5% free amino acids, are preferred.

For greatest use, the protein source can be lactose-free so it can be used for lactose intolerant patients.

When choosing a protein source, it may be optimal to first consider the biological value of the protein, with the highest biological values being found in casein, whey, lactalbumin, egg albumin, and whole egg proteins. Next, the cost can be considered, the lowest cost with the best biological value being the best combination.

The dietary formulation or supplement may also include a carbohydrate. The source of carbohydrate may be any simple monosaccharides, disaccharides (e.g. maltose and sucrose), oligosaccharides, polysaccharides, or complex carbohydrates. Examples include fructose, dextrose, glucose, maltodextrin, corn syrup and corn starch. Carbohydrate sources which may be utilized in the formulation of the invention include hydrolyzed or nonhydrolyzed starches. Combinations of such carbohydrate sources can also be used.

The dietary formulation or supplement may also include omega-9 fatty acid. Omega-9 fatty acids are a family of unsaturated fatty acids which have in common a carbon-carbon double bond in the n-9 position; that is, the ninth bond from the end of the fatty acid. Omega-9 fatty acids are common components of animal fat and vegetable oil. Without limitation, examples of omega-9 fatty acids are oleic acid (9-octadecenoic acid), eicosenoic acid (11-eicosenoic acid), mead acid (5,8,11-eicosatrienoic acid), erucic acid (13-docosenoic acid), and nervonic acid (15-tetracosenoic acid). Oleic acid is the main component of olive oil and other monounsaturated fats, and euric acid is found in rapeseed, wallflower seed and mustard seed. Preferably, the saturated fatty acids found in fish oil which increase bad cholesterol LDL are avoided in the dietary formulation. By using only $C_{20}$ or longer omega-3 fatty acids such as DHA and/or EPA, one will provide an optimal formula for improving triglyceride, LDL, and HDL cholesterol by lowering triglyceride and LDL and raising HDL. Adding non-omega-6 monounsaturated fatty acids like oleic acid can further improve lipid metabolism.

The dietary formulation or supplement can also be made in powder form by increasing the percent total solids of the formula, using procedures well known to those skilled in the art. The concentrate or powder can then reconstituted for feeding by adding water (tap or deionized-sterilized water).

Emulsifiers may be added for stability purposes, e.g., emulsifiers such as soybean phospholipids. This may be desired for parenteral products. Emulsifying agents for oil emulsions are generally phospholipids of natural, synthetic or semi-synthetic origin. A variety of suitable emulsifying agents are known in the art. Examples of suitable emulsifying agents include, but are not limited to, egg phosphatidylcholine, egg lecithin, L-α-dipalmitoyl phosphatidylcholine (DPPC), DL-α-dipalmitoyl phosphatidylethanolamine (DPPE), and dioleoyl phosphatidylcholine (DOPC). In accordance with the present invention, the total concentration of triglycerides as well as free fatty acids in the emulsifier should be low in order to minimize the contribution to the total oil concentration of the emulsion. In one embodiment of the present invention, the total concentration of triglycerides as well as free fatty acids in the emulsifier is less than about 3.5%.

In one embodiment of the present invention, lecithin is used as the emulsifying agent in the lipid emulsions. Alternatively, egg lecithin can be used as the emulsifying agent. Egg lecithin containing 80-85% phosphatidyl choline and less than about 3.5% of fat can also be used as an emulsifying agent. One skilled in the art will appreciate that other components may be present in the egg lecithin without adversely affecting the emulsifying properties. For example, the egg lecithin may contain one or more of phosphatidyl ethanolamine, lysophosphatidyl choline, lysophosphatidyl ethanolamine, sphingomeylin and other natural components.

The oil emulsions according to the present invention typically contain between about 0.5% and about 5% (w/v) emulsifying agent. In one embodiment of the present invention, the emulsion contains between about 0.6% and about 2% (w/v) emulsifying agent. In another embodiment, the emulsion contains between about 0.8% and about 1.8% (w/v) emulsifying agent. In another embodiment, the emulsion contains between about 1.0% and about 1.5% (w/v) emulsifying agent. In another embodiment, the emulsion contains between about 1.2% (w/v) and about 1.4% emulsifying agent.

The ratio of lecithin to source oil in the emulsion is important in determining the size of the oil globules formed within the emulsion. In one embodiment, the ratio of lecithin to source oil is between about 1:4 and about 1:20. In one embodiment of the present invention, the ratio is between about 1:4 and about 1:18. In another embodiment, the ratio is between about 1:4 and about 1:15. In another embodiment, the ratio is between about 1:4 and about 1:10.

Flavoring may also be added to the dietary formulation to make it more palatable for enteral use. Flavoring can be in a form of flavored extracts, volatile oils, chocolate flavoring, peanut butter flavoring, cookie crumbs, vanilla or any commercially available flavoring.

The dietary formulation or supplement of the invention may also contain a stabilizer such as λ-carrageenan. λ-carrageenan increases the viscosity of the formula without forming a gel structure, thus retarding the precipitation of insoluble calcium and phosphorus salts if included in the formula. Xanthan gum or other standard stabilizers may also be used as a stabilizer in the same fashion as λ-carrageenan. /

The dietary formulation or supplement in accordance with the present invention can further comprise additional components such as, antioxidants, chelating agents, osmolality modifiers, buffers, neutralization agents and the like that improve the stability, uniformity and/or other properties of the formulation.

Suitable antioxidants that can be added include, but are not limited to, alpha-tocopherol (vitamin E) and tocotrienols. As is known in the art, tocotrienols are a natural blend of tocotrienols and vitamin E extract concentrated from rice bran oil distillate, which have an antioxidant activity similar to that of alpha-tocopherol (vitamin E). Tocotrienols have a similar structure to vitamin E and contain three double bonds in the carbon side chain of the molecule.

When used in an emulsion, the concentration of antioxidant added to the emulsion is typically between about 0.002 and about 1.0% (w/v). In one embodiment, the concentration of antioxidant used in the emulsion is between about 0.02% and about 0.5% (w/v).

In one embodiment of the present invention, tocotrienols are added as an antioxidant. In another embodiment, about 0.5% (w/v) tocotrienols are added. In still another embodiment, vitamin E is added is added as an antioxidant. In one embodiment, about 0.02% (w/v) vitamin E is added.

Oil emulsions can further comprise a chelating agent to improve the stability of the emulsion and reduce the formation of oxidized fatty acids. Suitable chelating agents are known in the art and are those that are generally recognized as safe (GRAS) compounds. Examples include, but are not limited to, EDTA. In one embodiment of the present invention, the emulsion comprises EDTA. In another embodiment, the emulsion comprises concentrations of EDTA between about $1 \times 10^{-6}$ M and $5 \times 10^{-5}$ M.

Container design is also an important factor when manufacturing fat emulsions. If the emulsion is packaged in glass, it is preferably done in a container that is filled with nitrogen before the actual emulsion is added. After addition of the emulsion, the glass container can be filled again with nitrogen to remove dead space when the cap is affixed. Such nitrogen filling prevents peroxide formation. If the product is packaged in plastic, a DEHP-free container that is gas impermeable is preferred. Preferably the container also has the appropriate overwrap to minimize peroxide formation in the lipids as well as leaching of the plasticizer from the container into the product itself. In addition, if plastic is used, it is desirable to have a desiccant in with the bag as well as an indicator that notes if there is a air leak in the overwrap. Preferably the container is also latex-free.

An osmolality modifier can also be incorporated into the dietary formulation (e.g. emulsion) to adjust the osmolality to a value suitable for parenteral administration. Amounts and types of osmolality modifiers for use in parenteral formulations are well-known in the art. An example of a suitable osmolality modifier is glycerol. The concentration of osmolality modifier typically ranges from about 2% to about 5% (w/v). In one embodiment of the present invention, the amount of osmolality modifier added is between about 2% and about 4%. In another embodiment, the amount of osmolality modifier added to the formulation is between about 2% and about 3%. In another embodiment, about 2.25% (w/v) glycerol is added as an osmolality modifier. The final product should preferably be isotonic so as to allow infusion of the formulation through either a central or peripheral venous catheter.

One skilled in the art will understand that the pH of the formulation can be adjusted through the use of buffers or neutralization agents. Emulsions with pH values close to physiological pH or above have been shown to be less prone to fatty acid peroxidation. One skilled in the art will appreciate that the pH of the formulation can be adjusted through the use of an appropriate base that neutralizes the negative charge on the fatty acids, through the use of an appropriate buffer, or a combination thereof. A variety of bases and buffers are suitable for use with the formulations of the present invention. One skilled in the art will appreciate that the addition of buffer to the emulsion will affect not only on the final pH, but also the ionic strength. High ionic strengths may negatively impact the zeta potential of the emulsion (i.e. the surface charge of the oil globules) and are, therefore, not desirable.

Selection of an appropriate buffer strength to provide a suitable pH and zeta potential as defined herein is considered to be within the ordinary skills of a worker in the art.

In one embodiment of the present invention, the pH of the formulation is adjusted using sodium hydroxide. In another embodiment, the pH is adjusted with a buffer. In another embodiment, the buffer is a phosphate buffer. In another embodiment, both sodium hydroxide and a phosphate buffer are added to the formulation.

The final pH of the formulation is typically between about 6.0 and about 9.0. In one embodiment of the present invention, the pH of the formulation is between about 7.0 and about 8.5. In another embodiment, the pH of formulation is between about 7.0 and about 8.0.

The dietary formulation described herein can further comprise a therapeutic agent beyond the various components already discussed. A "therapeutic agent" as the term is used herein refers to a physiologically or pharmacologically active substance that produces a localized or systemic therapeutic effect or effects in animals and refers generally to drugs, nutritional supplements, vitamins, minerals, enzymes, hormones, proteins, polypeptides, antigens and other therapeutically useful compounds. The dietary formulation may also further comprise a diagnostic agent.

The oil emulsions in accordance with the present invention can be prepared by any number of conventional techniques known to those skilled in the art. In general, the core lipid is first mixed with the emulsifier and the antioxidant, if one is being used. The emulsion is then prepared by slowly adding this oil phase into water with constant agitation. If an osmolality modifier is being used, it is added to the water prior to mixture with the oil phase. The pH can be adjusted at this stage, if necessary, and the final volume adjusted with water, if required.

In one embodiment, the dietary formulation is provided in the form of food oil suitable for oral administration. Examples of formulations suitable for oral administration include, but are not limited to food oil present in, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, health bars, confections, animal feeds, cereals, yogurts, cereal coatings, foods, nutritive foods, functional foods and combinations thereof.

Soft gel or soft gelatin capsules may be prepared, for example by dispersing the oil emulsion formulation in an appropriate vehicle to form a high viscosity mixture. This mixture is then encapsulated with a gelatin based film using technology and machinery known to those in the soft gel industry. The industrial units so formed are then dried to constant weight.

It will be recognized that any known means of producing gel capsules can be used in accordance with the present invention. Compressed tablets can be prepared by, for example, mixing the formulation with dry inert ingredients such as carboxymethyl cellulose and compressing or molding in a suitable machine. The tablets optionally can be coated or scored and can be formulated so as to provide slow or controlled release of the pharmaceuticals therein. Other formulations include lozenges comprising the formulation in a flavored base, usually sucrose and acacia or tragacanth.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

If plasticizers are used, they are preferably previously dissolved in an organic solvent and added in solution form. Examples of plasticizers include, but are not limited to diethyl phthalate, diethyl sebacate, triethyl citrate, cronotic acid, propylene glycol, butyl phthalate, dibutyl sebacate, castor oil and mixtures thereof. As is evident, the plasticizers may be hydrophobic as well as hydrophilic in nature. Plasticizers can aid in nutritional composition release.

Administration of the dietary formulations and/or dietary supplements described herein can be used for overall nutrition, and/or for reducing the levels of omega-6 fatty acids in an individual. Such a reduction is useful in reducing inflammation in an individual. As such, one aspect of the invention relates to a method for reducing inflammation in an individual. The method comprises administration of the dietary formulation and/or dietary supplement described herein. Administration is for a period of time necessary to produce the desired reduction in inflammation. Any of the specific formulations described herein can be used to produce a reduction in inflammation. The optimal formulation for use is to be determined on a case by case basis for each individual, and will depend upon factors the circumstances specific to the individual (e.g. the specific desired results, previous diet, the specific physical condition of the individual). A reduction in inflammation resulting from the administration can be determined by the skilled practitioner. Guidance and examples of measuring inflammation, is provided herein.

Inflammation which is to be reduced may be ongoing (e.g. from a pre-existing condition or disease) or expected (e.g., from exposure to a substance, increase risk of disease development, or expected procedures such as surgical procedures). Ongoing inflammation may be the result of, or the cause of, a disease or disorder, or may merely be associated with a disease or disorder of the individual. As such, aspects of the present invention relate to a variety of methods of treatment and/or prevention of a variety of conditions in an individual. Without limitation, such conditions include inflammatory diseases or disorders, fatty liver disease, obesity, diabetes, metabolic syndrome. In other embodiments, the dietary formulations are used to minimize the risk of infection, to reduce the fat content of a liver in a liver donor, and/or to treat essential fatty acid deficiency.

In one embodiment, the method of the invention comprises identification of a subject in need of reduction of inflammation, followed then by administration of the dietary formulation or supplement of the invention. A subject in need is a subject who has detectable adverse inflammation (e.g. detectable by one or more means known in the art, some of which are described herein), or a subject who has a disease or pathology or condition associated with adverse inflammation. A subject in need can also be a subject with an increased likelihood (e.g., from a genetic pre-disposition, behavioral, or environmental effects) for development of a condition resulting from, producing, or associated with adverse inflammation. A subject in need, may further be a subject in need of a liver transplant, or a subject who plans to donate a liver, or have another operation, or is otherwise at increased risk for infection (e.g., is immunocompromised). Such a subject can be determined by the skilled practitioner through known means of diagnosis.

As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. For methods of prevention, a subject to be administered the dietary formulation is generally a subject at risk for an inflammatory condition due to genetic predisposition, diet, exposure to disorder-causing agents, exposure to pathogenic agents, and the like. The term "treat" or "treatment" refer to both therapeutic treatment and prophylactic or preventative measures, wherein the object is to prevent or slow down the development or spread of disease or symptoms. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also refer to prolonging survival as compared to expected survival if not receiving treatment.

The term "subject", "individual", and "patient" are used interchangeably herein, and refer to an animal, especially a mammal, for example a human, to whom treatment, with a composition as described herein, is provided. The term "mammal" is intended to encompass a singular "mammal" and plural "mammals," and includes, but is not limited: to humans, primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears.

The term "inflammatory disease or disorder" as used herein, refers to any disorder that is either caused by inflammation or whose symptoms include inflammation, or is otherwise associated with inflammation. One such inflammatory disorder caused by inflammation is septic shock, and an inflammatory disease whose symptoms include inflammation is rheumatoid arthritis. Inflammation is associated with a number of diseases or disorders, for example, neurodegenerative diseases, cardiovascular disease or disorders, and infectious diseases. The inflammatory disorders of the present invention include but are not limited to: diabetes-associated nephropathy and retinopathy, protein wasting, muscle fatigue or inflammation, coronary artery disease, inflammatory bowel disease, atherosclerosis and other cardiovascular diseases, Alzheimer's disease, myocarditis, cardiomyopathy, pancreatitis, HIV disease and AIDS, complication of AIDS or cancer therapy, celiac disease, cystic fibrosis, acute endocarditis, pericarditis, hepatitis, Systemic Inflammatory Response Syndrome (SIRS)/sepsis, adult respiratory distress syndrome (ARDS), asthma, rheumatoid arthritis, osteoarthritis, systemic lupus erythematosis, airway hyperresponsiveness (AHR), bronchial hyperreactivity, chronic obstructive pulmonary disease (COPD), congestive heart failure (CHF), inflammatory complications of diabetes mellitus, inflammatory bowel disease (CROHN's disease and/or ulcerative colitis) to either induce remission and/or prevent relapse, metabolic syndrome, non-alcoholic fatty liver disease, end stage renal disease (ESRD), and dermatitis. Another inflammatory condition which can be treated is major burns (e.g. second or third degree burns). In one embodiment, the major burns cover more than 20% body surface area. Another inflammatory condition which can be treated is traumatic brain injury (e.g. with a Glasgow Coma Score less than 8). Multiple trauma as well as any critical illness producing APACHE III scores of greater than 10 can also be treated. Another condition which can be treated by the methods of the present invention is receipt of a stem cell transplant or a bone marrow transplant.

"Inflammation" or "inflammatory symptoms" refers to one or more biological and physiological sequelae including: vasodilatation; increased vascular permeability; extravasation of plasma leading to interstitial edema; chemotaxis of neutrophils, macrophages and lymphocytes; cytokine production; acute phase reactants; C-reactive protein (CRP); increased erythrocyte sedimentation rate; leukocytosis; fever; increased metabolic rate; impaired albumin production and hypoalbuminemia; activation of complement; and stimulation of antibodies.

As used herein, "cardiovascular disease" includes diseases associated with the cardiopulmonary and circulatory systems including but not limited to ischemia, angina, edematous conditions, artherosclerosis, CHF, LDL oxidation, adhesion of monocytes to endothelial cells, foam-cell formation, fatty-streak development, platelet adherence, and aggregation, smooth muscle cell proliferation, reperfusion injury, high blood pressure, and thrombotic disease.

As used herein, a "symptom" of an inflammatory condition includes physical symptoms (pain, edema, erythema, and the like) associated with a particular inflammatory condition, and/or biomarkers associated either generally with inflammation or particularly with a specific inflammatory condition.

In one embodiment, a method of reducing the level of an inflammatory biomarker in a subject that correlates to an inflammatory condition is provided. The method comprises administering to the subject the dietary formulation described herein, wherein the formulation is administered in an amount sufficient to reduce the level of the inflammatory biomarker.

"Inflammatory biomarkers that correlate with an inflammatory condition, " and also "inflammatory biomarkers" include, but are not limited to CRP, cytokines associated with inflammation, such as members of the interleukin family, including IL-1 through IL-17 that are associated with inflammation, TNF-alpha; B61; certain cellular adhesion molecules, such as for example, e-selectin (also known as ELAM), sICAM, integrins, ICAM-1, ICAM-3, BL-CAM, LFA-2, VCAM-1, NCAM and PECAM; neopterin; serum procalcitonin; leukotriene, thromboxane, and isoprostane.

In particular, elevated levels of CRP are associated with cardiovascular diseases and disorders, infectious diseases, such as, myocarditis, cardiomyopathy, acute endocarditis, or pericarditis; SIRS; diabetes; metabolic syndrome; muscle fatigue, injury or inflammation; and systemic inflammation.

Other inflammatory biomarkers that correlate with inflammatory disease include: Elevated levels of IL-6, sTNFr2 and CRP are associated with type II diabetes, muscle inflammation and ESRD; elevated levels of cellular adhesion molecules are associated with systemic inflammation; elevated levels of IL-1 and TNF-alpha are associated with IDDM and NDDM associated inflammation; elevated levels of IL-10 and IL-6 are associated with SIRS; elevated levels of neopterin are associated with SIRS; elevated levels of procalcitonin are associated with systemic inflammation. (e.g., detecting a reduction in levels of inflammatory biomarks or proteins associated with inflammation)

Other proteins or markers associated with inflammation include serum amyloid A protein, fibrinonectin, fibrinogen, leptin, prostaglandin E2, serum procalcitonin, soluble TNF receptor 2, elevated erythrocyte sedimentation rate, and elevated white blood count, including percent and total granulocytes (polymorphonuclear leukocytes) monocytes, lymphocytes and eosinophils.

In one embodiment, the inflammatory biomarker is selected from the group consisting of C-reactive protein (CRP), interleukin-1-alpha (IL-1-alpha), interleukin-1-beta (IL-1-beta), interleukin-6 (IL-6), soluble TNF receptors I and II, oxidative metabolites of protein, carbohydrate, fat, DNA, and elevated white blood cell count (WBC).

The dietary formulation and dietary supplements of the invention are to be administered over an effective regimen. As the term is used herein, the term "regimen" is used to refer to the systematic plan of administration of the dietary formulation. As such, the regimen includes the dose per specific administration, the time course of each administration, the time period between individual administrations, the time period over which a specific dose is used, and coordination of other therapies or medications or procedures. Dosage may beneficially be adjusted over time. For example, initial dosage may contain extremely low to no arachidonic acid, to rapidly reduce extremely high levels in an individual. Following the desired reduction, the amounts of arachidonic acid may be increased to levels that will maintain the desired levels in the individual. The individual can be monitored over the course of the regimen to track fatty acid levels, and the dosage can be adjusted accordingly.

"effective regimen", which is to say an "effective amount" is administered over an effective course (a sufficient dose or amount over a sufficient period of time) to achieve a final concentration in the body sufficient to produce the desired results (e.g. of reducing inflammation). Such an "effective regimen" leads to a statistically significant reduction in one or more symptoms of inflammation. An effective regimen may result in a reduction of one or more markers of disease, and/or may result in complete prophylaxis or elimination of one or more symptoms. More specifically there may be at least about 30%, at least about 50%, at least about 70%, at least about 80%, and at least about 90% reduction in the markers or symptoms as measured by convention means (e.g., in the levels of inflammatory biomarkers associated with inflammation or an inflammatory condition, and/or a reduction in one or more symptoms associated with inflammation such as pain and/or edema associated with inflammation).

By "amount sufficient to reduce the level of inflammatory biomarker" is meant that the dietary formulation is administered in an "effective regimen", which is to say an "effective amount" is administered over an effective course (a sufficient dose or amount over a sufficient period of time) to achieve a final concentration in the body sufficient for reducing inflammation as measured by a reduction in the amount of an inflammatory biomarker.

An "effective amount" is an amount sufficient to produce beneficial or desired results in a subject. An effective amount can be administered in one or more administrations. For purposes of this invention, an effective regimen is a course of administration of an effective amount of the dietary formulation or supplement sufficient to ameliorate, stabilize, reverse, slow or delay the progression or onset of the disease or disorder, e.g. fatty liver disease, essential fatty acid deficiency, obesity, diabetes, cardiovascular disease, or inflammatory disorder. The beneficial or desired results can be measured by monitoring the reduction in or disappearance of one or more symptoms of the disease or disorder. One of skill in the art will recognize that an effective amount does not require complete recovery or complete prevention of a symptom, but merely a significant, sustainable, measurable reduction. Preferably one or more symptoms are reduced by at least about 30%. In one embodiment, one or more symptoms are reduced by at least about 50%. In one embodiment, one or more symptoms are reduced by at least about 70%, at least about 80%, or at least about 90% measurable reduction in a symptom.

Amelioration of symptoms due to inflammation can be quantified by one or more assays known in the art. For example, a statistically significant reduction in CRP levels and/or reduction in cytokines such as, but not limited to interleukins 1-17 (IL 1-17) associated with inflammation; and TNF-alpha. A clinical analysis which tracks a combination of two or more such markers of inflammation may also prove useful in analysis of symptom reduction. Such assays are well known to those skilled in the art (see for example, U.S. Pat. No.'s 5,688,656; 6,040,147; 6,180,643; 5,993,811; 6,103,702; 6,203,997, 5,496,832; 5,780,237 and U.S. Patent application publications 2005/0137253 and 20010007022, which are herein incorporated by reference in their entirety).

C-reactive protein (CRP) serves as an exemplary marker for systemic inflammation. See U.S. Pat. No. 6,040,147. In humans CRP levels are elevated during inflammatory disorders such as infection, trauma, surgery, tissue infarction, and in IDDM patients without macrovascular disease. The magnitude of the increase varies from about 50% to as much as 100-fold during systemic inflammation (Gabay, C., et al., New Engl. J. Med. 340: 448-454, 1999). Recent evidence has shown that CRP is also a risk factor for cardiovascular disease and stroke where inflammation plays an important role (Lagrand, W. K., et al, Circulation 100: 96-102, 1999). Most CRP production is from hepatocytes in response to pro-inflammatory cytokines, especially interleukin-6 and 1.quadrature.(Ganter, U., et al., EMBO J. 8: 3773-3779, 1989), although macrophages have also been reported to release CRP (Dong, Q, et al, J. Immunol. 156: 481504820, 1996).

Surrogate markers of inflammation in diabetic patients include glycosylated hemoglobin (HbA1c) and advanced glycation endproducts (AGEs) that are formed from glycosylated hemoglobin and related compounds. Additional biomarkers of inflammation in diabetes include arachidonate (5,8, 11,14 eicosatetraenoic acid, an essential omega-6 highly unsaturated fatty acid that provides both critical structural properties to membranes, and which, when released from phospholipids, functions as the primary substrate for eicosanoid (prostaglandin, thromboxane, leukotriene) synthesis. Arachidonate has been linked to many processes that are implicated in type-2 diabetes, such as insulin release from the pancreas, insulin action in skeletal muscle and insulin sensitivity.

In one embodiment, the disease to be prevented or treated is fatty-liver disease. As such, another aspect of the invention relates to a method for preventing or treating fatty-liver disease in a subject. The method comprises administering an effective regimen of the dietary formulation or dietary supplement described herein. The method may further comprise determination of a subject in need of such treatment or prevention, followed by beginning the course of administration. As used herein "fatty-liver disease" refers to a disease wherein fat (hepatocytes) is excessively accumulated in the liver and can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is about 10% (100 mg/g wet weight) or more of the wet weight of hepatic tissue. A significant reduction in the liver fat content of a fatty liver is another indicator of amelioration of symptoms. Any reduction in fat content is beneficial. Preferably the reduction is at least 5%, at least 10%, at least 20%, at least 30%, at least 40%, at least 50%, at least 60%, at least 70%, at least 80%, or at least 90%.

Fatty liver disease is generally detected by observation of elevated serum levels of liver-specific enzymes such as the transaminases ALT and AST, which serve as indices of hepatocyte injury, as well as by presentation of symptoms, which include fatigue and pain in the region of the liver, though definitive diagnosis often requires a biopsy. Fatty-liver disease is also associated with parenteral nutrition; this disease includes both biochemical, i.e., elevated serum aminotransferases, bilirubin, and alkaline phosphatase, and histologic alterations such as steatosis, steatohepatitis, lipidosis, cholestasis, fibrosis, and cirrhosis.

Detectable, sustained reduction in serum levels of such transaminases ALT and AST, and/or of aminotransferases, bilirubin, and alkaline phosphatase would serve as another indicator of amelioration of symptoms by administration of the dietary formulation of the present invention.

In vivo animal models of varied diseases and disorders are known in the art and may be used to determine the efficacy of the dietary formulations, or treatment protocols. For example, U.S. Pat. No. 6,103,702 describes a model for systemic inflammatory response syndrome (SIRS) and sepsis, where the efficacy of treatment in vivo may be determined through monitoring the level of TNF-a in tissues such as spleen and liver or in serum; U.S. Pat. Nos. 6,193,957; 6,051,566; 5,080,899, 6,180,643, 6,028,208 and U.S. Pat. App. Nos. 20010000341, 20010006656 describe models and protocols for determining the efficacy of treatments for conditions associated with pulmonary or respiratory inflammation; U.S. Pat. No. 5,789,652 is directed to a non-insulin dependent diabetic rat which can be used to determine the efficacy of test compounds in the treatment of the diabetes; models for fatty liver and excessive weight gain with insulin resistance are also known.

A "sustained reduction" is a statistically significant, repeatedly observable detected reduction, over an established period of time (e.g. days, weeks, months).

The duration of treatment can be chronic, e.g. for the rest of the life of the subject, or it can be administered episodically. In some cases (e.g. acute conditions) it may be possible to discontinue administration of the dietary formulation at some point without recurrence or worsening of symptoms. Prolonged administration may be necessary in other circumstances (e.g. chronic conditions) to produce a continued therapeutic effect. Appropriate dosages and administration regimens can readily be determined by one skilled in the clinical arts.

Enteral feeding literally means using the gastrointestinal tract for the delivery of nutrients, which includes eating food, consuming oral supplements and all types of tube feeding. When the formulation is in the form of a dietary supplement (food oil) suitable for oral administration, the formulation should provide about 5-60% of total energy expenditure of the subject in terms of calories in the form of the fatty acids specified herein.

Methods of administering oil emulsions to patients for total enteral nutrition are known in the art. The routes most often used are naso-gastric tubes (NGT) and percutaneous endoscopic gastrostomy (PEG) tubes. Other routes that are increasingly being used include naso jejunal and jejunostomy feeding, which may be the only feasible route if it is not appropriate to feed via the stomach. A skilled artisan understands dosages necessary for total enteral nutriton. The dosage is to provide sufficient energy to provide energy balance which generally ranges from 15-40 kilocalories/kg weight of the patient. The duration of the administration can be either short term (e.g. days to several weeks or months) or long-term (e.g. years to permanent).

Total parenteral nutrition (TPN), is the practice of feeding a person intravenously, circumventing the gut. Methods of administering oil emulsions to patients for total parenteral nutrition (PN) applications or therapeutic benefit are known in the art. Typically the emulsions are administered by infusion over a suitable period of time. The preferred method of delivering TPN is with a medical infusion pump. A sterile bag of nutrient solution, between 500 mL and 4 L is provided. The pump infuses a small amount (0.1 to 10 mL/hr for pediatric applications or at rates of 40cc/hour up to 120 cc/hour, depending on fluid requirements, for adults) continuously in order to keep the vein open. Feeding schedules vary, but one common regimen ramps up the nutrition over a few hours, levels off the rate for a few hours, and then ramps it down over a few more hours, in order to simulate a normal set of meal times.

For treatment of diseases and disorders, e.g., essential fatty acid deficiency and inflammatory diseases or disorders, obesity, etc., or for methods for increasing immunity or minimizing the risk of infection, any form of administration known in the art may be used. When total enteral or parenteral nutrition is used, the formulation preferably also contain all essential amino acids, as well as essential vitamins and minerals to insure that the patient is obtaining necessary nutrients. When the formulation is in the form of a dietary supplement (food oil) suitable for oral administration, the formulation may provide about 5-60% of total energy expenditure of the subject in terms of calories.

In treating a liver transplant donor, the formulation or supplement is administered prior to the donation of the liver. Preferably, administration is for a period of time sufficient to reduce the fat content of a liver, e.g. the formulation or supplement may be given orally or enterally for four to six weeks, or intravenously for four to five days prior to liver donation. Other administration protocols can be used and can readily be determined by one skilled in the clinical arts. Subjects may also be treated prior to a surgical procedure, e.g. the formulation or dietary supplement may be given orally or enterally for four to six weeks, or intravenously for four to seven days prior to surgery. Other administration protocols can be used and can readily be determined by one skilled in the clinical arts. Administration to the donor may also be performed after liver transplant during postoperative recovery. This can occur even when the donor did not receive administration prior to donation.

A liver transplant recipient can be likewise administered the formulations of the present invention, pre-operatively, and/or pos-operatively, as described herein.

Aspects of the invention further relate to a method for treating a subject prior to, and/or following, receiving a surgical procedure. Such methods are analogous to the other methods of treatment described herein.

The present invention additionally provides for kits containing the dietary formulations for administration to a subject. The kit would provide an appropriate dosing regimen for a prescribed period.

The kits of the invention comprise one or more packages or containers containing the dietary formulation in combination with a set of instructions, generally written instructions, relating to the use and dosage of the formulation. The packages containing the formulation may be in the form of unit doses or pharmacy bulk packages. The doses may be packaged in a format such that each dose is associated, for example, with a day of the week. There may also be associated with the kit a notice in the form prescribed by a governmental agency regulating the manufacture, use or sale of biological products, which notice reflects approval by the agency of manufacture, use or sale for human or animal administration.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%. When "0%" is used to describe the amount of a component, it is understood that this includes situations where only trace amounts of the component are present.

All patents, patent applications, and publications identified in this document are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The following examples are not intended to limit the present invention in any way.

EXAMPLES

Example 1

Fish Oil is Sufficient to Prevent Essential Fatty Acid Deficiency

Materials and Methods

Nutritional model. Animal protocols complied with the NIH Animal Research Advisory Committee guidelines and were approved by the Children's Hospital Boston Animal Care and Use Committee.

Forty 6-8 week old C57/B16 mice (Jackson Laboratories, Bar Harbor, Me.) were housed in a barrier room. After three days of acclimatization, they were divided into two main groups, ad libitum (group I) and pair fed (group II). Both groups were further divided into four subgroups with five animals each. These four subgroups were fed identical diets that only differed in fat composition (FIG. 6 depicting Table 1). Water was provided ad libitum and none of the groups received any additional source of nutrition. Chow with three different percentages of fat (1%, 5%, 10% menhaden/fish oil) were utilized for the first three subgroups and the fourth subgroup was fed 5% soybean oil chow (Dyets Incorporated, Bethlehem, PA) (FIG. 7 depicting Table 2).

Corn starch was utilized to ensure isocaloric diets. The 5% fish oil diet was taken as the caloric point of reference and as such, the control soybean oil content was set to 5%. In this manner, the margin of discrepancy in caloric density between all diets was minimized to less than or equal to 0.5 kcal/g. The menhaden oil diets had 3.4, 3.6, and 3.9 kcal/g in the 1%, 5%, and 10% chow, respectively, and the 5% soybean oil diet had 3.6 kcal/g.

To avoid differential food aversion bias amongst the animals and to examine possible metabolic differences, we chose a parallel pair fed and ad libitum feeding model. Our technique of pair feeding was based on previously described methods.[24] Briefly, all groups ate ad libitum the first day and the amount of chow ingested was measured. Of the four subgroups, the group with the least amount of chow ingested was identified. To allow for increasing nutritional requirements of growth, 10% was added onto this total to determine the amount of food to be administered to all groups for the following day. The time course of the experiment was nine weeks. The ad libitum groups had access to unlimited chow at all times and the amounts eaten were recorded every three days. Both pair fed and ad libitum groups were weighed every three days.

Phlebotomy. At day 0 and weeks 3, 6, and 9 (end date), blood was drawn from all animals by retro-orbital puncture and placed in serum separator tubes. Isoflurane was used as general anaesthetic during these procedures. Blood was centrifuged at 800 rpm for 10 minutes after which the plasma was separated and stored at -80° C.

Fatty acid analysis. Fatty acid analysis was performed on all plasma samples, as previously described.[20] Briefly, after fatty acids were extracted from plasma, phospholipid (PL) and triglyceride (TG) fractions were isolated by solid-phase chromatography. These fatty acids were subsequently saponified and transmethylated using boron trifluoride-methanol. The obtained fatty acid methyl esters were then digitally quantified utilizing a gas chromatograph (Hewlett-Packard 5890, Series II, Palo Alto, Calif.).

Statistical analysis. For statistical analysis of food intake in kilocalories and grams, we performed a paired t-test (Sigmastat 3.0). Calculations were also performed analyzing the amount of double bonds, using a Holm-Sidek comparison (two-way ANOVA).

From the fatty acid analysis profile, we excluded a total of eight fields from our relevant data as outliers using the Extreme Student Deviate (ESD) statistic within the upper $5^{th}$ percentile ($\alpha$=0.05), as described by Rosner.[25] Four baseline PL EPA, one baseline TG MA, one 6-week TG triene-tetraene ratio, and two PL triene-tetraene ratios for baseline and 3-week, respectively, were eliminated from the data set before statistical analysis was conducted. Due to loss of PL data in the fatty acid analysis of the baseline 10% ad libitum fish oil group, the retrieved values were insufficient to allow proper statistical analysis. Therefore, we decided to take the average of all baseline animals, not yet influenced by any means, to establish a realistic PL baseline threshold for further comparisons over time within that group.

Indicator fatty acids, including MA, AA, EPA, and DHA, and the triene-tetraene ratio were compared between the fish oil groups and controls using a three-way repeated-measures mixed model analysis of variance (ANOVA). This statistical approach accounts for the multiple measurements over time within the same animals (correlated data) and the varying values of animals in the treatment groups.[26] Diet and feeding mode (pair fed or ad libitum) were treated as between-subjects factor and time (baseline, 3, 6, and 9 weeks) as a within-subjects factor. Several different covariance structures were compared to determine optimal model fit, including compound symmetry and autoregressive, and a diagonal structure fit the data best according to the Bayesian information criterion (BIC).[27] To account for multiple pairwise group comparisons, a Bonferroni adjusted p-value was used to protect against committing false positive errors (type I errors). Data for the triene-tetraene ratio for TG and PL are presented in terms of the estimated marginal means and standard errors. Statistical analysis was performed using the GLM (General Linear Model) procedure in the SPSS software package (version 15.0, SPSS Inc., Chicago, Ill.). All reported p-values are two-tailed. Five mice were randomized to each condition (diet group×mode=4×2=8 conditions) for both TG and PL (total N=80 samples). A power analysis indicated that the sample sizes of five mice in each of the diet groups and five controls measured at each of the time points for each of the feeding modes would provide 80% power to detect a mean difference of 0.05 in the triene-tetraene ratio between the fish oil diet groups and soybean controls using mixed-model ANOVA with repeated-measures (version 6.0, nQuery Advisor, Statistical Solutions, Saugus, Mass.).

Results

There are three types of fatty acids important in mammalian cells: omega-3, omega-6, and omega-9 fatty acids. They serve an array of tissue functions and are critically important in all membrane-associated processes. Furthermore, fatty acids produce numerous bioactive metabolites that mediate the inflammatory response, vasodilatation/vasoconstriction, and the regulation of platelet aggregation.[1,2] Their nomenclature refers to the distance of the first double bond from the terminal methyl group of the acid. The omega-9 fatty acid, oleic acid (OA), can be derived from simple precursors in mammals. Mammals cannot insert double bonds at position-3 and -6 to produce $\alpha$-linolenic (ALA) and linoleic acid (LA), respectively (FIG. 1). Therefore it is an absolute requirement that the omega-3 and omega-6 fatty acids be obtained from the diet. The omega-3 and omega-6 fatty acids are also termed as polyunsaturated fatty acids (PUFA) since they contain two or more double bonds in their carbon chain. EFA deficiency (EFAD) results in biochemical changes in the structure and metabolism of all plasma and tissue lipids, which can eventually lead to clinical symptoms. EFAD results from low dietary intake, severe malabsorption, and/or increased physical requirements such as growth.[5] In 1971, Holman described the symptoms of EFAD in rats and other mammalian species, including primarily impaired growth and dermatitis, and secondarily steatosis, renal toxicity, pulmonary abnormalities, and increased metabolic rate.[6]

The major biochemical changes of EFAD are decreased AA and increased Mead acid (MA), the latter being a downstream product of oleic acid (OA). Desaturase enzymes display differential activity in the order of preference omega-3>omega-6>omega-9. As a result, conversion of OA to MA (omega-9) only occurs when there are low dietary levels of both ALA (omega-3) and LA (omega-6). This metabolic switch is seen as a compensatory mechanism to maintain the number of double bonds in cell membrane fatty acids. Therefore, elevated MA in conjunction with a lowered AA is indicative of a pathologic, EFAD process.[7,8]

During EFAD, omega-3 and omega-6 fatty acids are diminished. LA is normally converted to AA (20:4), a tetraene. To compensate for this deficiency, OA is converted to MA (20:3n-9), a triene (FIG. 1). A determination of the relative amount of MA to AA, called the triene-tetraene ratio, can be made and when this ratio rises above 0.2, a diagnosis of EFAD can be supported. This threshold was first set to 0.4, based on the appearance of clinical EFAD symptoms above that ratio. However, more recently a ratio not greater than 0.2 has been suggested because average ratios in Western populations, with high omega-6 diets, were found to be only 0.1±0.08.[9] The minimum ALA concentrations in the diet have been reported to be 0.2-1% of total caloric intake in adults and 0.5% in infants and young children.[2,10-12] Standard minimum intake to meet LA requirements is set to 1% of total caloric intake in animal studies.[6,13] Human studies have shown that estimated optimal daily requirements of LA are 1-3% of total caloric intake, increasing proportionally with growth.[2,14-17]

The objectives of this study were to establish biochemical standards and essential fatty acid profiles for diets with differing lipid compositions. We hypothesized that menhaden oil, although deficient in LA, contains sufficient amounts of EPA, DHA, and AA to prevent biochemical and clinical EFAD.

Animals

Figure 2A:
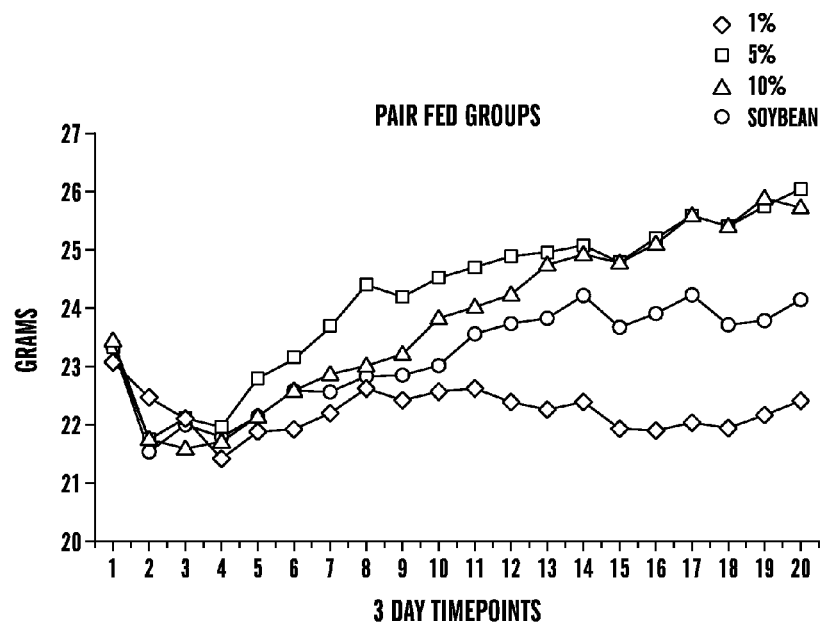
FIGS. 2A and 2B are graphical representations of data which indicate the average weight for pair fed (FIG. 2A) and ad libitun (FIG. 2B) groups through the nine week experiment. X-axis: 3 day time points; Y-axis: Grams. Diets are 1%, 5%, and 10% menhaden oil diets and soybean diet.
Figure 2B:
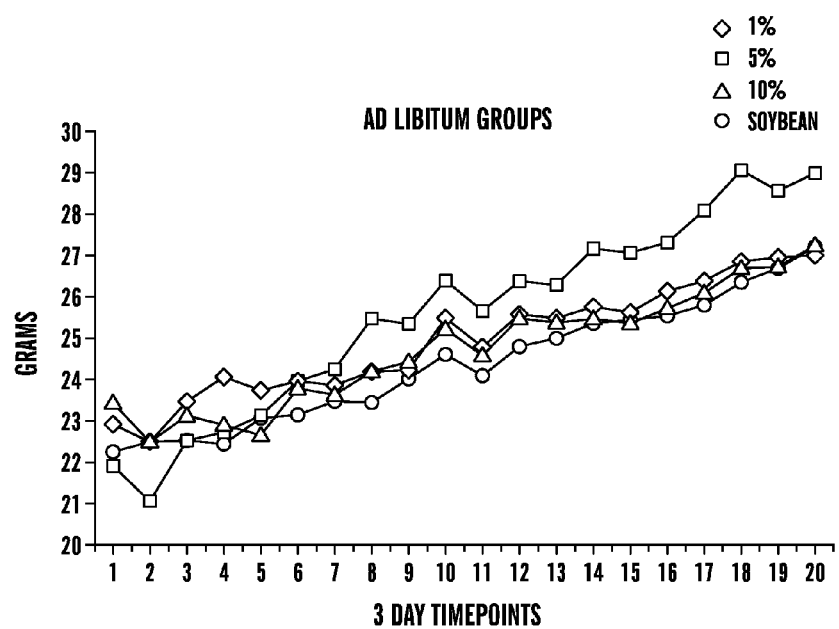
Figure 3:
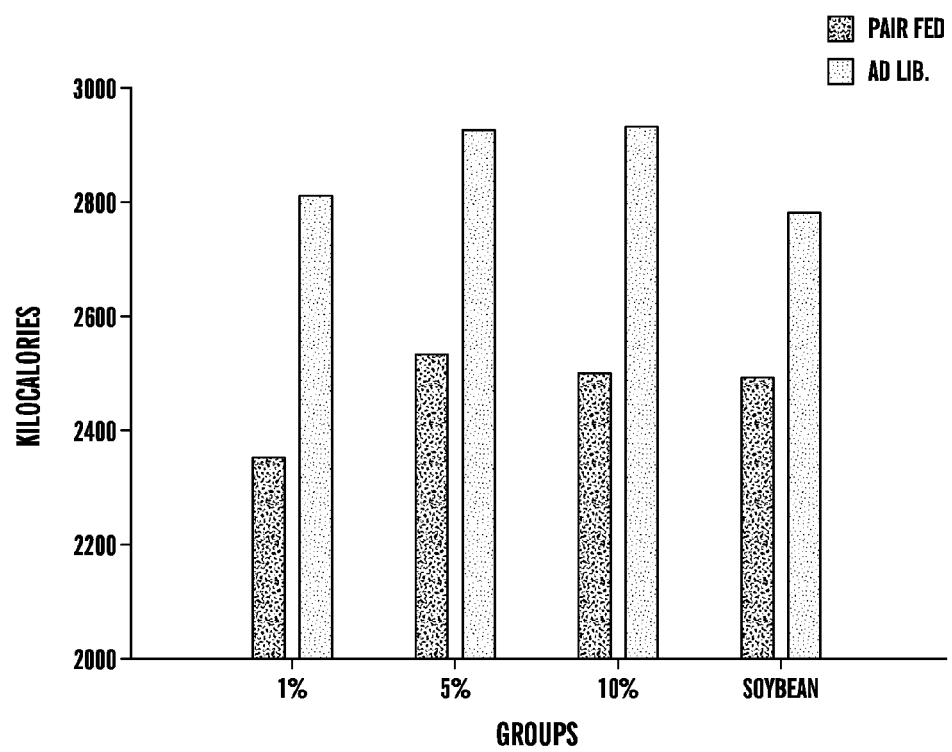
FIG. 3 is a graphical representation of data which indicates the total food intake in kilocalories by pair fed and ad libitum groups. X axis: diet groups; Y-axis: Kilocalories. Diets are 1%, 5%, and 10% menhaden oil diets and soybean diet.

Throughout the nine week experiment, all animals in both the pair fed and ad libitum groups were clinically well. None of the animals showed any signs of EFAD, such as dermatitis, alopecia, or infections. Regarding the most important clinical EFAD parameter, weight status, all groups but the 1% pair fed group gained weight. In both pair fed and ad libitum groups, there was a transient weight loss at the initiation of dietary treatment (baseline). This weight loss was more severe and more prolonged in the pair fed groups (FIG. 2). Total average weight differences and standard deviations after nine weeks compared to baseline for the pair fed 1%, 5%, and 10% fish oil groups and the 5% soybean group per mouse were: $-0.68\pm2.02$, $+2.78\pm1.60$, $+2.24\pm2.10$, and $+0.82\pm0.81$ g, respectively. For the ad libitum groups, weight change was: $+4.12\pm1.4$, $+7.1\pm3.14$, $+3.74\pm1.39$ and $+4.88\pm0.81$ grams for the same groups. In the ad libitum groups, significantly higher values overall were found compared to pair fed groups for both intake in grams or intake converted to kilocalories (P=0.002 for grams, P=0.002 for kilocalories). In the pair fed groups, the 10% fish oil diet was usually the diet with the most residual chow remaining. Food intake of the pair fed 5%, 10% fish oil groups and soybean 5% groups was relatively isocaloric, whereas the 1% fish oil group intake was slightly decreased (FIG. 3).

Caloric Efficiency

Figure 4:
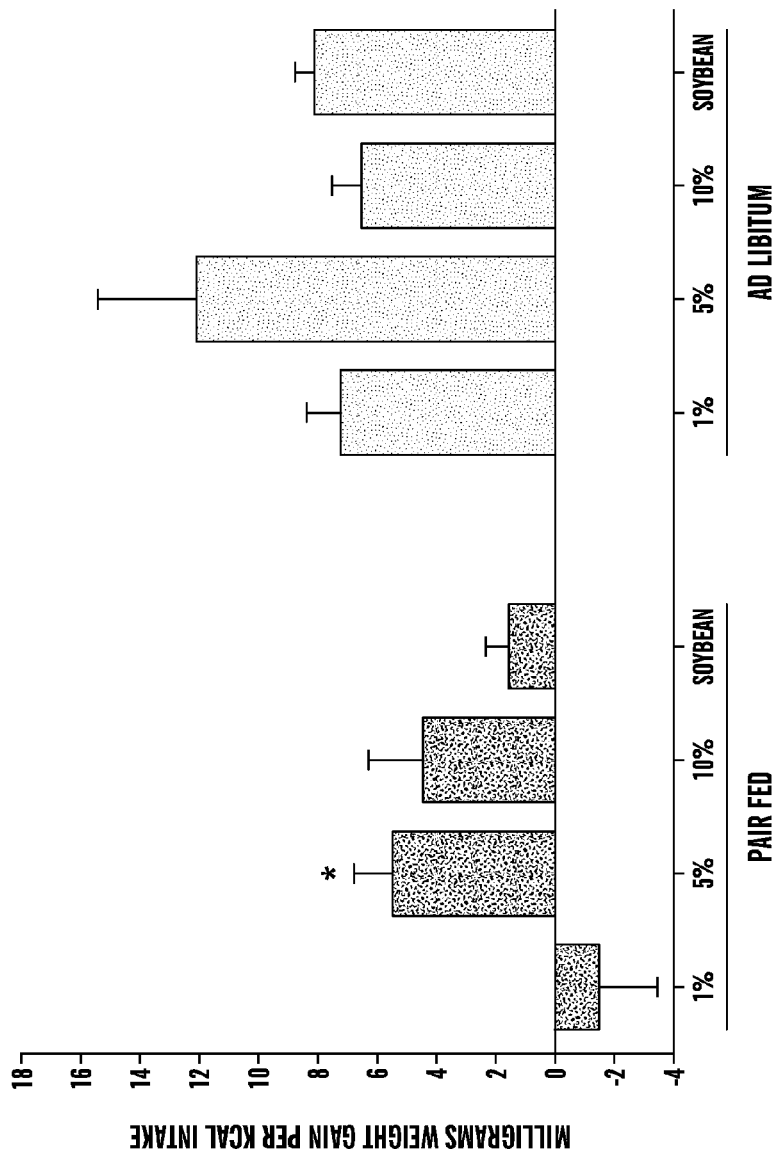
FIG. 4 is a graphical representation of data which indicates the caloric efficiency in milligrams weight gain per kilocalorie per mouse. X axis: pair fed and ad libitum fed diet groups; Y-axis: mg weight gain per kcal intake. Diets are 1%, 5%, and 10% menhaden oil diets and soybean diet.

To look at growth parameters for each individual diet over the nine week experimental period, we divided the total weight gain per group by the total intake in kilocalories of that group. In this manner, we established a quantification of caloric efficiency per corresponding diet in milligrams per kilocalorie (FIG. 4). In the pair fed groups, there was a negative number for the 1% fish oil diet ($-1.45$ mg/kcal), reflecting the weight loss of this group reported earlier. The pair fed 5% fish oil group showed the highest caloric efficiency at 5.5 mg/kcal, followed by the 10% group at 4.5 mg/kcal. The soybean control diet showed a caloric efficiency of 1.6 mg/kcal. There was a statistically significant difference among all diet groups (P=0.027, One way ANOVA) and only the 5% fish oil was significantly higher when compared to the soybean oil control (P=0.042, t-test).

The ad libitum group had improved caloric efficiency among all diets. The 5% fish oil group again scored the highest with 12.1 mg/kcal. The 1% fish oil and soybean oil groups had caloric efficiencies of 7.4 and 8.8 mg/kcal, respectively, moderately increased over pair fed, whereas the 10% was 6.4 mg/kcal, minimally increased over pair fed. No statistical significance was shown.

Fatty Acid Analysis

The fatty acid analysis (FAA) on the blood samples taken every three weeks allowed us to compare physiological changes in the triglyceride (TG) and phospholipid (PL) levels of the relevant FA as well as the triene-tetraene ratios over time (FIGS. 8 and 9 (Table 3)).

Arachidonic acid (AA): At baseline, all groups had levels of approximately 0.25 nmol/ml, without any statistical difference between groups. In the serum, TG analysis of the pair fed group, the 1% group AA levels stayed relatively high at weeks 3 and 6, where the 5% and 10% groups decreased (FIG. 8 depicting Table 3a). These values remained elevated in the soybean group with a peak at 6 weeks. After 6 weeks, all fish oil groups had a significantly lower concentration of AA than the soybean group. After 9 weeks, all fish oil groups maintained that lower level, although only the 10% fish oil group remained significantly lower.

In the PL analysis, there was a gradual decline of AA levels in the 1% fish oil group as seen in the TG fraction pair fed group (FIG. 9 depicting Table 3b). At 9 weeks, all fish oil groups again plateaud at the same level (0.11-0.14 nmol/ml) although the 1% fish oil group was the only group to show statistical significance with time (p=0.01 for 3 wks compared to 9 wks). The AA level in the soybean group rapidly elevated and maintained high levels from the $3^{rd}$ week onward. As in the TG fraction, there were statistically significant differences between fish oil diets and the soybean control diet between weeks 3 and 9.

Mead acid (MA): Typically, MA levels are very low or undetectable. This is supported by the MA levels in all four subgroups at baseline being, or approaching, zero. The TG fraction in the pair fed animals suggest that the 1% fish oil group has statistically significant increasing MA levels over the entire study period while the 5% fish oil group has a slight increase at 9 weeks.

In the PL fraction, the 5% fish oil group had an unusually elevated MA level at baseline. We saw a delayed but significant increase in MA levels from 6 weeks onward in the 1% fish oil group with consequential statistical significance when compared to the other groups, where minimal MA concentrations were present at all times.

Eicosapentaenoic acid (EPA): EPA is one of the two downstream omega-3 FA that is directly provided by fish oil but not present in the soybean oil diet. Soybean oil contains the omega-3 FA α-linolenic acid (18:3) (ALA) which is converted by means of desaturation and elongation to produce EPA.

The TG fraction pair fed profile showed an EPA increase in all fish oil groups and a decrease in the group fed the soybean diet. The soybean oil group had significantly lower levels of EPA than all fish oil groups from baseline to endpoint. Calculated over time, the 5% fish oil group was significantly higher than both 1% and 10% because of slight declines in EPA levels of the 1% and 10% groups at 9 weeks.

As expected, we found decreasing EPA levels in the PL fraction in the pair fed group for the soybean diet and again, like in the TG fraction, 5% fish oil EPA levels climbed faster than both the 1% and 10% diets. There was a decrease in EPA concentrations in animals fed fish oil diets in each of the EPA profiles at the 9 week timepoint. At that same timepoint, the EPA in the soybean groups dropped to very low levels.

Docosahexaenoic acid (DHA): DHA is the other omega-3 FA derived from ALA, downstream from EPA (FIG. 1). We found an unusually low baseline level of DHA in the TG fraction in the pair fed group for the 5% fish oil diet after which this group's DHA concentration increased to significantly higher levels than all other diets. The soybean diet DHA concentration decreased steadily over time. At 6 weeks, DHA levels in the 1% fish oil group were statistically higher than the soybean group, and eventually at the 9 week endpoint, all fish oil groups reached similar levels, statistically higher than the soybean group (FIGS. 8 and 9 (Table 3)).

Figure 5A:
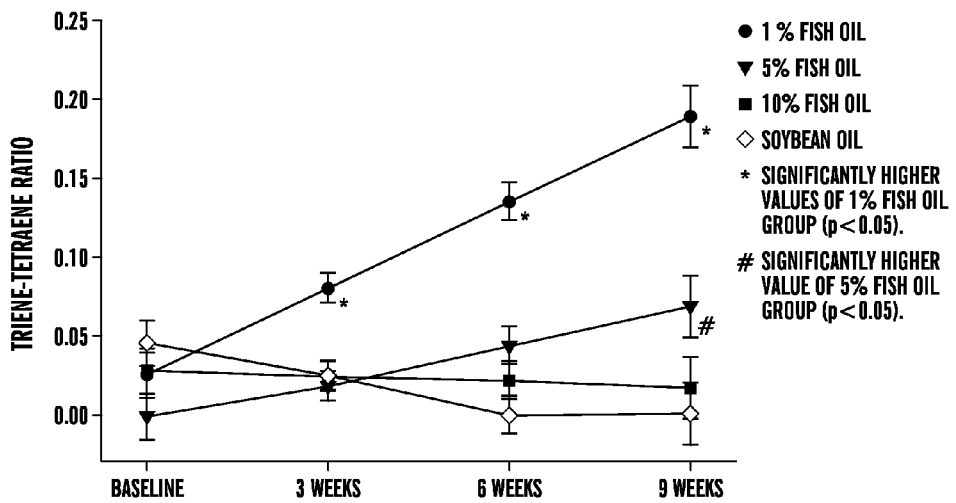
FIGS. 5A and 5B are graphical representations of data which indicate triglyceride analysis pair fed (FIG. 5A) and phospholipid analysis pair fed (FIG. 5B) triene-tetraene ratios over the 9 week experiment. X axis:weeks of experiment; Y-axis: Triene-tetraene ratio. Diets are 1%, 5%, and 10% menhaden oil diets and soybean diet.

Triene-tetraene ratio (TT): This ratio of MA and AA is seen as the gold standard defining EFAD. In the TG fraction of the pair fed group, the TT ratio declined to zero in the soybean diet group and remained stable in the 10% fish oil group. The TT ratio in the 1% fish oil group increased steadily up to 0.22 nmol/ml surpassing the critical 0.2 nmol/ml threshold for biochemical determination of EFAD. The TT ratio in the 5% fish oil group increased gradually and never exceeded the EFAD threshold. Significantly higher ratios in the 1% fish oil group from 3 weeks on and the increase in the 5% fish oil resulted in statistical significance at 9 weeks (FIG. 5a & FIG. 8 depicting Table 3a).

Figure 5B:
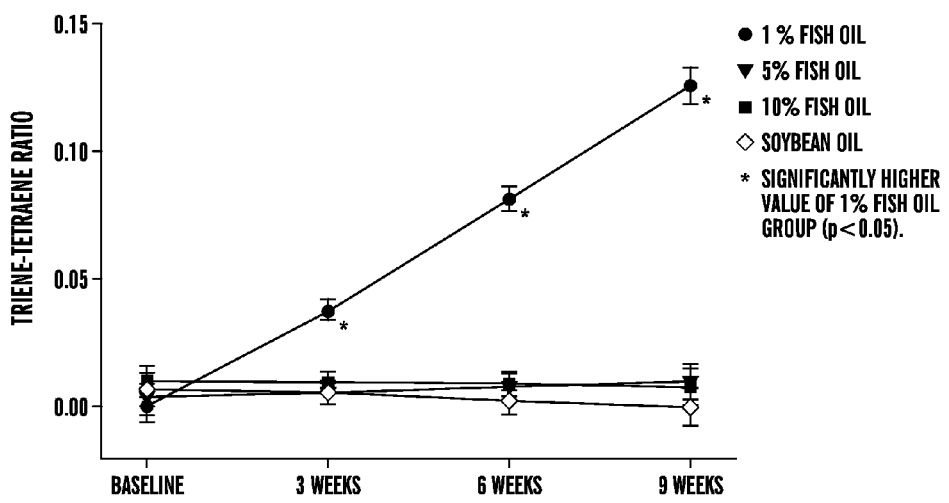

In the PL fraction of the pair fed cohorts, all groups except the 1% fish oil displayed very low ratios during the entire experiment. The 1% fish oil group had significantly higher ratios, although levels did not reach the nmol/ml (FIG. 5b & FIG. 9 depicting Table 3b).

Double Bonds

From the FA profile, we calculated the average plasma concentration of double bonds by taking the mole percentages where applicable and multiplying by the number of double bonds of that specific fatty acid. The double bond fatty acids include 16:1, 18:1, 18:2, 18:3, 20:3n-6, 20:3n-9, 20:4, 20:5, 22:4, 22:5n-3, 22:5n-6, and 22:6 (FIG. 1). The sum of these values gives the double bond concentration in each of the 1%, 5%, 10% fish oil and soybean oil groups, for both the pair fed and ad libitum animals after the 9 week feeding experiment (FIG. 10A depicting Table 4a). The statistical analysis is shown (FIG. 10B depicting Table 4b).

There was no significant difference between the pair fed and ad libitum groups ($p=0.800$). The average number of double bonds remained the same despite the vast difference in calorie intake between the two groups. When examining the different diets within the pair fed group, we found that the 10% fish oil group was significantly different from the others ($p<0.05$). Calculations between the other diets resulted in no statistical difference, with the largest p-value ($p=0.612$) in the comparison of 1% fish oil vs. soybean, showing their close resemblance. In the ad libitum group there was a similar trend in diet comparison. Again the measurements for the 10% fish oil group showed clear statistical significance when compared to the other diets ($p<0.05$).

Parenteral nutrition (PN) is a life saving treatment for thousands of patients with severe bowel malformations or insufficient gastrointestinal absorptive function.[28] However, long term use of this therapy is associated with many complications, among which PN-associated liver disease (PNALD) is the most important. Recent studies have shown that lipid metabolism is altered by its route of administration; intravenous infusion bypasses normal enterocyte targeting of lipids in the bowel, causing fat accumulation in the liver and predisposing the patient to PNALD.[29] The properties of fish oil have been investigated for a large spectrum of clinical conditions. Based on animal models, omega-3 fatty acid lipid emulsions derived from fish oil may prevent hepatic injury through inhibition of de novo lipogenesis.[23] However, the administration of omega-3 fatty acids is described only as a diet supplement and has never been indicated as the sole source of fat calories because of the concern for the development of EFAD. Gura et al reported on an EFA-deficient, PN-dependent patient that was treated with omega-3 lipid emulsions (OmegavenTM) because of inability to tolerate the conventional omega-6 soybean emulsion due to soy allergy; biochemical markers improved within a week after the start of therapy and EFAD was successfully treated.[22] More recently, two infants were treated in the same manner, this time in an attempt to counteract PN-associated cholestasis, and again no signs of EFAD were noted and both patients experienced resolution of cholestasis.[23]

Despite these promising preliminary results, disputes about the presumed lack of EFA content in fish oil remain. Indeed, the manufacturer of one such product has stated that the menhaden oil used does not contain enough omega-6 fatty acids to prevent EFAD.[30] This continued skepticism, although recently refuted by the clinical evidence, urged us to investigate the development of EFAD utilizing different lipid sources and thereby establish biochemical standards for the menhaden oil.

Multiple studies have been conducted regarding the metabolism of individual FA, EFAD, and EFA requirements. A review by Cunanne et al. reports about minimal LA and AA requirements separately as the sole sources of fat.[31] However, a comprehensive biochemical EFAD study of menhaden oil, which contains omega-3 FA EPA and DHA and small amounts of omega-6 FA LA and AA, has never been done. Nonetheless, it is increasingly warranted considering the growing clinical interest in the use of fish oil.

The energy percentages provided by omega-6 fatty acids (LA, AA) per diet are needed for adequate comparison to conventional requirement beliefs. By weight, menhaden oil contains 1.5% LA and 0.9% AA, whereas soybean oil contains 54.8% LA and 0% AA. Using the typical inspection data, we calculated the total energy provided by the different diets (FIG. 11 depicting Table 5). The relative amounts of omega-3 fatty acids have also been listed (FIG. 7 depicting Table 2).

For this experiment, a parallel set-up was chosen with treatment of the four diets by either pair feeding or ad libitum feeding technique. Pair feeding eliminates the variable of different food intake and ensures adequate metabolic comparison. The ad libitum feeding model allows us to determine whether fish oil decreases food intake and also serves as a control group. Remarkably, in the ad libitum groups, all fish oil groups took in more calories than the soybean oil group throughout the 9 week experiment, invalidating the concern that fish oil palatability would bias food intake.

Analysis of caloric efficiency is only valid when intake is standardized, which makes the ad libitum data inconclusive. A limitation of our pair feeding model is that the amount of chow given was based on chow weight per day, rather than chow calories per day. As a consequence, although in the 5%, 10% fish oil and soybean oil groups the pair feeding was successful (2510 kcal±1%), the 1% fish oil group had decreased caloric intake (2347 kcal), resulting in the only report of weight loss in the experiment. When looking at the ad libitum 1% fish oil group, we see that these animals actually eat the most by weight, perhaps to compensate for diminished calorie intake and/or the lack of EFA.

In the pair fed groups caloric efficiency is higher in the 5% and 10% fish oil groups when compared to soybean oil. The most appropriate comparison is between the 5% fish oil group and the control soybean oil group, since they share the same caloric value (3.6 kcal/g). Here we found the only instance of statistical significance in caloric efficiency improvement in 5% fish oil compared to the soybean oil diet (P=0.042). Therefore, fish oil clearly proves to have higher caloric efficiency in this experiment. This is also true, although less conclusive, for the ad libitum groups (FIG. 4).

Soybean oil is generally considered the lipid source of choice with respect to growth. We have shown that fish oil actually enhances growth when compared to soybean oil (FIG. 2). This contradicts earlier reports about the negative effect of fish oil on growth in human infants; this negative effect is attributed to the mechanism that omega-3 fatty acids decrease conversion of LA to AA, an important omega-6 derivative that mediates the secretion of several hormones associated with growth.[32-35] It is important to note that omega-3 fatty acids in these cases were used as supplements as opposed to the sole source of fat as in our study. One important consequence is the vast difference in relative amounts of LA to AA intake when fish oil is a supplement to usual LA intake versus fish oil administration as the sole source of dietary fat. The principal effect of EPA on AA levels in serum PL membranes in the former instance is through inhibition of the conversion of dietary LA to AA with a much smaller effect on AA levels that come through the diet.

The fatty acid analysis was divided into the TG and PL fractions. The fatty acid profile of serum TG primarily reflects adipose tissue composition postabsorptively and dietary intake postprandially while the profile of serum PL reflects hepatic metabolism of fatty acids. Therefore, TG data are more rapidly reflective of the diet because of the inherent delay of hepatic metabolism in the PL data. However, TG composition is more variable since it is highly dependent on dietary intake. PL content is much less diet-dependent and thus, most nearly reflects whole body membrane lipid composition and is the better indicator of EFAD.

At the start of the experiment, all animals were weaned from standard chow (Prolab Isopro RMH 3000, PMI Nutrition. International, Brentwood, MO) which contains adequate levels of both omega-3 and omega-6 fatty acids according to conventional requirements. The switch to the 'extreme' experimental diets becomes apparent in all profiles after the three week 'wash out' period during which the physiologic effects of diet therapy are realized.

As noted prior, the pair fed fatty acid analysis is the most relevant because of standardization of caloric intake, and as such, the ad libitum data is not shown. That said, ad libitum data were very similar to pair fed, deviating only through accelerated data differences due to the faster metabolic switch resulting from increased food intake. Some discrepancies with the pair fed groups could be attributed to the different caloric intake between all diets rather then the fatty acid content. For example, the TG analysis of AA in the ad libitum group has a more evident increase to over 0.8 nmol/ml when compared to the pair fed TG. Also, the PL ad libitum group shows similarly decreasing levels in AA for all fish oil groups, although they stabilize at approximately 0.08 nmol/ml as opposed to 0.13 nmol/ml seen in the pair fed fish oil groups. Both these discrepancies could be attributed to higher caloric intake in the ad libitum groups, accelerating the metabolic switch induced by the chow change at baseline (Table 3).

Omega-3 and omega-6 fatty acids are competitive substrates for the same enzymes, Δ6 and Δ5 -desaturases and elongase, and through this competition they inversely affect each other's tissue levels. However, omega-3 fatty acids, although competitive with LA, reduce requirements for omega-6 fatty acids and attenuate symptoms usually attributed to omega-6 fatty acid deficiency.[31] This particular characteristic gives fish oil an important advantage in overcoming the risk of EFAD development and is confirmed by our biochemical data.

Remarkable in the AA profiles of both TG and PL fractions is that only the soybean group displays significantly higher levels after the 'wash out' period despite vast differences in AA content amongst the fish oil diets (FIGS. 8 and 9 (Table 3)). Together with the direct provision of AA, enough LA is converted to AA to in each of the three fish oil concentrations to maintain stable levels. As expected, the levels of AA are much higher in the soybean oil group with higher levels of LA and no EPA to inhibit the conversion of LA to AA.

The increasing levels of MA in the 1% fish oil group signal the development of EFAD with a delay in PL levels when compared to the TG fraction. Additionally, at nine weeks, the MA increase in the 5% fish oil group for the TG fraction levels reveals instability. This suggests that 5% fish oil as the sole source of fat might be insufficient to prevent conversion to MA, although still sufficient to maintain the triene-tetraene ratio within normal range and not statistically different from the 10% fish oil ratio.

EPA profiles show an increase in all fish oil groups and a decrease in the soybean groups. The 5% fish oil levels of EPA climbed significantly faster than the other fish oil groups in both TG and PL fractions. This is also seen in DHA TG levels, although PL levels do not statistically support that data. These findings are unexpected and could be correlated with our caloric efficiency data suggesting highly effective fatty acid metabolism for the 5% fish oil diet. The DHA data show only a slight increase and decrease for fish oil and soybean PL, respectively. The more profound changes in EPA profiles compared to DHA can be attributed to the higher concentration of EPA in fish oil and to the higher baseline levels for DHA after weaning from standard chow. Notably, the EPA levels, and to a lesser extent DHA, only in the TG analysis, drop to very low levels in the soybean group when compared to baseline. This is likely a consequence of the minimal amounts of ALA accompanied by large amounts of LA in the soybean diet. It is known that EPA metabolites serve as important anti-inflammatory eicosanoids and cytokines, where AA metabolites are thought to be pro-inflammatory.' Consequently, administration of soybean oil may create a pro-inflammatory environment. This has been suggested in clinical studies where children supplemented with conventional soybean oil lipid emulsions may be more susceptible to steatohepatitis and PNALD.[23]

The triene-tetraene ratio illustrates whether the decrease of AA reported in all fish oil groups has pathologic consequences (i.e. development of EFAD). Because none of the AA levels showed any significant difference, the ratio solely depends on the conversion of OA to MA. The data clearly shows that 1% fish oil does not contain sufficient essential fatty acids (omega-3 and omega-6 fatty acids) to prevent EFAD (FIG. 5), a conclusion that is supported by the growth data. The 10% fish oil group never showed any clinical or biochemical signs of EFAD, suggesting that it can be safely used as the sole source of fat. The 5% fish oil seems to display a pivotal point in the spectrum between 1% and 10%. Examining caloric efficiency, this group outscores all others. In addition, considering that its triene-tetraene ratio is well below the 0.2 nmol/m1 threshold, this concentration appears sufficient. However, in the TG data, the triene-tetraene ratio for the 5% fish oil group is increased significantly compared to both 10% fish oil and the control soybean group, and the ratio should stabilize throughout the experimental period to ensure adequate EFAD prevention. The increase at nine weeks in the TG analysis could suggest a tendency towards the development of EFAD, although PL levels which are more relevant do not show this trend. This presumably reflects the small amount of AA in the 5% diet which is still sufficient to maintain the triene-tetraene ratio after hepatic metabolism as better reflected in the PL.

The fact that the amount of double bonds were not significantly different between pair fed and ad libitum groups is striking, considering the large differences in caloric intake. More importantly, however, is the observation that 1% fish oil and soybean oil show the same number of double bonds. The 5% and 10% fish oil groups have a higher number of double bonds because EPA and DHA, with more double bonds, are directly provided by fish oil. The body must store those fatty acids because the ability to retroconvert and thereby diminish double bond number is not as effective as the elaborate system for elongation and desaturation from the LA and ALA precursors. This suggests that the body needs a certain amount of double bonds to maintain desired membrane fluidity, but supplemental provision of EPA and DHA can lead to further increases of fluidity, which is one the proposed mechanisms for improved membrane function. In soybean oil, there is enough LA to convert to AA to produce the desired number of double bonds. Conversely, in 1% fish oil there is not enough essential 18-carbon precursors to convert, resulting in the body switching to MA which, together with AA decrease, is the measure of EFAD.

The concentration threshold for fish oil as the sole source of fat in prevention of EFAD in mice lies between 5% and 10%. This signifies an omega-6 fatty acid requirement between 0.314% and 0.629% of dietary energy when given in this combination of LA and AA, roughly half of what is conventionally believed (1%). This is likely due to the small amounts of AA present in fish oil that have been found to be three times more effective than LA in multiple studies.[13] Therefore this requirement would presumably be even lower if omega-6 fatty acids were entirely provided by AA. AA is usually tightly regulated because it is a source of bioactive eicosanoids and prostaglandins. Our data suggests that fish oil does not harmfully suppress AA levels due to enzyme competition but rather are due to insufficient AA concentrations in the diet. Although the AA levels in the fatty acid profiles of the PL fraction shows no statistical difference when compared to each other, the 1% fish oil group is the only group that shows significantly lowering values over time comparing weeks 3 and 9 (FIG. 9 depicting Table 3b). This suggests that there are enough omega-6 fatty acids to satisfy the regulatory needs of AA in 5% and 10% but not in 1% fish oil. This statement is validated by the double bond data that indicates that the significantly increasing conversion to MA in the 1% fish oil group is likely a compensatory response to maintain the total number of double bonds (i.e. optimal membrane fluidity) when both omega-3 and omega-6 fatty acids fail to suffice.

Infants have high requirements of EFA for growth and development and there are suggestions that there are beneficial effects of AA supplementation to fish oil.[35,36] However, the consequence of fish oil to lower AA levels has generally been found when used as a supplement to much larger LA intake and was not seen in this study where fish oil was the sole fat. Furthermore, growth was actually enhanced by fish oil in this study, where reduced growth has been one of the undesired side effects of a lowered AA level with fish oil supplementation in infant formulas. Moreover, supplementation of AA could also partly diminish the anti-inflammatory advantages of fish oil administration when fish oil is provided as in this study. An ideal balance in this matter has to be pursued, but will always be highly dependent on clinical variables and individual patient needs. In conclusion, based on our biochemical data, 10% fish oil is likely to be adequate as the sole source of fat in PN to prevent and treat EFAD in infants.

Fish oil enhances growth through higher caloric efficiency. We have established a total omega-6 fatty acid requirement of between 0.314% and 0.629% of dietary energy, approximately half of the conventionally believed 1% as linoleic acid. This can be attributed to the presence of small amounts of arachidonic acid in fish oil, which has greater efficiency to meet omega-6 fatty acid requirements.

The references cited herein and throughout the specification are incorporated herein by reference.

References (Example 1)

1. Das. Essential fatty acids: biochemistry, physiology and pathology. *Biotechnology Journal*. Mar. 6, 2006 2006; 1:420-439.
2. Innis S M. Essential fatty acids in growth and development. *Prog Lipid Res*. 1991; 30(1):39-103.
3. Innis S M. Perinatal biochemistry and physiology of long-chain polyunsaturated fatty acids. *J Pediatr*. October 2003; 143(4 Suppl):S1-8.
4. Bistrian B R. Clinical aspects of essential fatty acid metabolism: Jonathan Rhoads Lecture. *JPEN J Parenter Enteral Nutr*. May-Jun 2003; 27(3):168-175.
5. Jeppesen P B, Hoy C E, Mortensen P B. Essential fatty acid deficiency in patients receiving home parenteral nutrition. *Am J Clin Nutr. July* 1998; 68(1):126-133.
6. Holman R. Essential fatty acid deficiency. *Prog Chem Fats Other Lipids*. Vol 9; 1971:275-348.
7. Smit E N, Muskiet F A, Boersma E R. The possible role of essential fatty acids in the pathophysiology of malnutrition: a review. *Prostaglandins Leukot Essent Fatty Acids*. October 2004; 71(4):241-250.
8. Farrell P M, Gutcher G R, Palta M, DeMets D. Essential fatty acid deficiency in premature infants. *Am J Clin Nutr*. August 1988; 48(2):220-229.
9. *Dietary Refernce Intakes for energy, carbohydrate, fiber, fat, fatty acids, cholesterol, protein and amino acids*: National academic press; 2005.
10. Bjerve K S, Fischer S, Alme K. Alpha-linolenic acid deficiency in man: effect of ethyl linolenate on plasma and erythrocyte fatty acid composition and biosynthesis of prostanoids. *Am JClin Nutr. October* 1987; 46(4):570-576.
11. Bjerve K S, Fischer S, Wammer F, Egeland T. alpha-Linolenic acid and long-chain omega-3 fatty acid supplementation in three patients with omega-3 fatty acid deficiency: effect on lymphocyte function, plasma and red cell lipids, and prostanoid formation. *Am J Clin Nutr. February* 1989; 49(2):290-300.
12. Bjerve K S, Mostad I L, Thoresen L. Alpha-linolenic acid deficiency in patients on long-term gastric-tube feeding: estimation of linolenic acid and long-chain unsaturated n-3 fatty acid requirement in man. *Am J Clin Nutr*. January 1987; 45(1):66-77.
13. Mohrhauer H, Holman R T. The Effect of Dose Level of Essential Fatty Acids Upon Fatty Acid Composition of the Rat Liver. *J Lipid Res. April* 1963; 4:151-159.
14. *Nutrition Recommendations*. Ottawa: Canada Health and Welfare, Health Protection Branch, Bureau of Nutritional Sciences; 1990.
15. *Diet Fats and Oils in Human Nutrition*. Vol Food and Nutrition Paper No. 3. Rome (Italy): FAO Expert Committee, 1977.
16. *Recommended Dietary Allowances*. 9th ed. Washington, D C: National Academy of Sciences; 1980.

17. Yamanaka W K, Clemans G W, Hutchinson M L. Essential fatty acids deficiency in humans. *Prog Lipid Res.* 1980; 19(3-4):187-215.
18. Lee S, Gura K M, Kim S, Arsenault D A, Bistrian BR, Puder M. Current clinical applications of omega-6 and omega-3 fatty acids. *Nutr Clin Pract.* August 2006; 21(4): 323-341.
19. Chen W J, Yeh S L. Effects of fish oil in parenteral nutrition. Nutrition. March 2003; 19(3):275-279.
20. Alwayn I P, Gura K, Nose V, et al. Omega-3 fatty acid supplementation prevents hepatic steatosis in a murine model of nonalcoholic fatty liver disease. *Pediatr Res.* March 2005; 57(3):445-452.
21. Clayton P T, Whitfield P, Iyer K. The role of phytosterols in the pathogenesis of liver complications of pediatric parenteral nutrition. *Nutrition.* January 1998; 14(1):158-164.
22. Gura K M, Parsons S K, Bechard L J, et al. Use of a fish oil-based lipid emulsion to treat essential fatty acid deficiency in a soy allergic patient receiving parenteral nutrition. *Clin Nutr.* October 2005; 24(5):839-847.
23. Gura K M, Duggan C P, Collier S B, et al. Reversal of parenteral nutrition-associated liver disease in two infants with short bowel syndrome using parenteral fish oil: implications for future management. *Pediatrics.* July 2006; 118 (1):e197-201.
24. Maynard L A L J. *Feeding experiments. The determination of digestibility.*: McGraw-Hill; 1962.
25. Rosner B. *Fundamentals of Biostatistics.* 6th ed: Thomson; 2005.
26. Khuri A I M T, Sinha B K. Statistical tests for mixed linear models. New York: John Wiley; 1998:95-118.
27. Schwarz G. Estimating the dimension of a model. *Ann. Stat.* Vol 6; 1978:461-464.
28. Wilmore DW, Dudrick S J. Growth and development of an infant receiving all nutrients exclusively by vein. *Jama.* Mar. 4, 1968; 203(10):860-864.
29. Javid P J, Greene A K, Garza J, et al. The route of lipid administration affects parenteral nutrition-induced hepatic steatosis in a mouse model. *J Pediatr Surg.* September 2005; 40(9):1446-1453.
30. Marcus A D. A Doctor's Push For Drug Pits Him Against Its Maker. *The Wall Street Journal.* November 13, 2006: A1, A15.
31. Cunnane S C. Problems with essential fatty acids: time for a new paradigm? *Prog Lipid Res.* November 2003; 42(6): 544-568.
32. Carlson S E, Cooke R J, Werkman S H, Tolley E A. First year growth of preterm infants fed standard compared to marine oil n-3 supplemented formula. *Lipids.* November 1992; 27(11):901-907.
33. Carlson S E, Werkman S H, Peeples J M, Cooke R J, Tolley E A. Arachidonic acid status correlates with first year growth in preterm infants. *Proc Natl Acad Sci U S A.* Feb. 1, 1993; 90(3):1073-1077.
34. Carlson S E, Werkman S H, Tolley EA. Effect of long-chain n-3 fatty acid supplementation on visual acuity and growth of preterm infants with and without bronchopulmonary dysplasia. *Am J Clin Nutr.* May 1996; 63(5):687-697.
35. Ryan A S, Montalto M B, Groh-Wargo S, et al. Effect of DHA-containing formula on growth of preterm infants to 59 weeks postmenstrual age. *Am J Human Biol.* 1999; 11(4):457-467.
36. Ling P R, Boyce P, Bistrian B R. Role of arachidonic acid in the regulation of the inflammatory response in TNF-alpha-treated rats. *JPEN J Parenter Enteral Nutr.* September-October 1998; 22(5):268-275.

Example 2

DHA and AA Alone are the Essential Fatty Acids

Background

LA and ALA are considered essential dietary nutrients in that all downstream FAs can be synthesized from these two 18-carbon precursors[12]. Among these downstream products are the highly physiologically relevant arachidonic acid (AA), docosahexaenoic acid (DHA) and eicosapentaenoic acid (EPA). These are considered to be critical metabolites because they are important eicosanoid and prostanoid precursors, thus mediating numerous physiological and biochemical processes in the human body. The omega-6 pathway leads to pro-inflammatory mediators while the omega-3s lead to anti-inflammatory pathways.

Essential fatty acid deficinecy (EFAD) results from low dietary intake of essential fatty acids or severe fat malabsorption, particularly in the setting of increased physical requirements such as growth[13]. In 1971, Holman described the symptoms of EFAD in rats and other mammalian species, including primarily impaired growth and dermatitis, and secondarily hepatic steatosis, renal toxicity, pulmonary abnormalities, and increased metabolic rate[14]. The major biochemical changes of EFAD are decreased AA and increased Mead acid (MA), the latter being a downstream product of OA. Desaturase enzymes display differential activity in the order of preference omega-3>omega-6>omega-9. As a result, conversion of OA to MA (omega-9) only occurs when there are low dietary levels of both ALA (omega-3) and LA (omega-6). This metabolic switch is seen as a compensatory mechanism to maintain the number of double bonds in cell membrane fatty acids. Therefore, elevated MA in conjunction with a lowered AA has been associated with the EFAD process[15,16].

During EFAD, omega-3 and omega-6 fatty acids are diminished, leading to a dearth of LA and its downstream products including the tetraene, AA (20:4). Additionally, lack of competition between OA and the omega-3 and omega-6 precursors for access to desaturase enzymes leads to excessive conversion of OA (the omega-9 precursor) to MA (20:3), a triene. A determination of the relative amount of MA to AA, called the triene-tetraene ratio, can be made and when this ratio rises above 0.2, a diagnosis of EFAD is supported[13,17]. The minimum ALA and LA concentrations in the diet have been reported to be 0.2% and 1% of total caloric intake respectively in adults and 0.5% for infants and young children[18-21]. Standard minimum intake to meet LA requirements is set to 1% of total caloric intake in animal studies [14,22].

Currently, standard lipid emulsions available in the U.S. (Intralipid, Liposyn) are soy based and thus contain predominantly omega-6 fatty acids. Other lipid emulsions developed in Europe (SMOF and Omegaven) contain considerable amounts of omega-3 fatty acids. The SMOF lipid emulsion is composed of 30% soybean oil and 15% fish oil, with the remaining oils provided as medium chain triglycerides (MCT) and olive oil. Omegaven is 100% fish oil. Our laboratory data in a PN-fed murine model of hepatosteatosis demonstrates significant liver injury with both intravenous standard lipid emulsion and SMOF[23]. Intravenous Omegaven, however, leads to prevention of hepatosteatosis in this mode[23]. Additionally, Omegaven has been shown to treat PNALD in numerous pediatric patients when substituted for the standard soy based emulsion[3,10,11]. Furthermore fish oil based emulsions are becoming increasingly expensive and their beneficial effects are likely to be improved with modifications of downstream products including altering the ratios of AA, EPA, and DHA, all of which now vary due to the source of the fish used to formulate the product. These requirements are also likely to vary from the very low birth weight infants to older children, since rapidly growing premature infants have higher requirements for essential fatty acids. In order to determine the optimal levels of these fatty acids, in a soy-free or fish oil-based lipid emulsion, we propose a series of experiments to explore the essentiality of DHA and AA in the absence of LA and ALA as a basis for developing lipid emulsion formulations specific for children. This is similar to the rationale for the use of specialty amino acid solutions in infant PN.

Results

Figure 12:
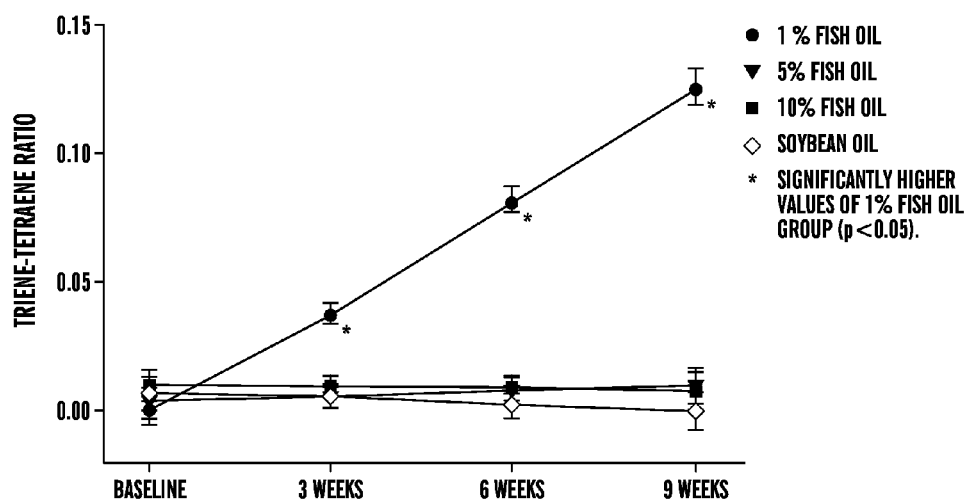
FIG. 12 is a line graph of data which indicates mice receiving fish oil as the sole source of fat calories over a 9 week period did not develop essential fatty acid deficiency and gained weight similarly to mice which received a normal diet.

Though Omegaven does contain small quantities of LA and AA, its use as the exclusive source of dietary fat poses a theoretical concern about the development of EFAD due to a reduced intake of LA. We performed studies in a murine model to further delineate the minimum intake of dietary fish oil to prevent EFAD. Forty mice were divided into two groups. In each group, four subgroups of five mice were fed approximately 1%, 5%, and 10% of enteral intake by weight (2,10, and 20% of total calories respectively) of their calories as fish oil diets or a control soybean diet for nine weeks. Blood was collected at four time points and fatty acid analysis was performed. Food intake and weight status were monitored. Mice receiving fish oil as the sole source of fat calories over a 9 week period did not develop EFAD and gained weight similarly (FIG. 12). These results indicate that the total omega-6 fatty acid requirement lies between 0.30% and 0.56% of total dietary energy, and is thus approximately half of the conventionally believed 1% LA requirement[24]. The presence of the small concentration of AA and significant content of DHA in fish oil is likely the mechanism by which EFAD is avoided in this situation.

We then utilized our animal model of EFAD to in a short term experiment to determine if DHA and AA may be the essential fatty acids. Specifically, individually caged animals were fed a fat free-PN solution placed in one water bottle per cage. Animals do not receive additional sources of hydration and nutrition. The study period was 19 days and mice were individually weighed every third day. Control mice received normal mouse chow and water ad libitum. Treated mice received daily fat equivalent to 5% of total calories intake via oral gavage. The fat dose is composed of AA, DHA plus hydrogenated coconut oil. AA and DHA are given in a 1:20 ratio similar to that in menhaden. Mice were placed in 6 groups of 5 animals. Group I (control) received chow, Group II received PN diet alone, Group III received PN plus fat that does not contain AA, DHA, or EFAs (100% hydrogenated coconut oil alone), Group IV received PN plus 4.2% of total fat calories composed of AA+DHA and 95.8% hydrogenated coconut oil, Group V received PN plus 42% of fat calories composed of AA+DHA and 78% hydrogenated coconut oil, and, Group VI received PN plus 84% of total fat calories composed of AA+DHA and 16% hydrogenated coconut oil. Hydrogenated coconut oil is added to each AA+DHA mixture to bring the total fat content to 5% of the daily caloric intake. After 19 days, the animals were sacrificed to determine FA profiles and liver histology. Preliminary data based on this experimental model is summarized in Table 6 below.

TABLE 6

| Group | Treatment | Serum Triene:Tetraene Ratio | Liver Triene:Tetraene Ratio |
|---|---|---|---|
| I | Chow | 0.03 | 0.04 |
| II | PN Alone | 0.84 | 1.02 |
| III | PN, 0% total fat as AA + DHA | 0.84 | 0.66 |
| IV | PN, 4.2% total fat as AA + DHA | 0.42 | 0.34 |
| V | PN, 42% total fat as AA + DHA | 0.02 | 0.03 |
| VI | PN, 84% total fat as AA + DHA | 0.00 | 0.00 |

These results demonstrate that when animals receive AA and DHA more than 2.1% of total calories (group V) or 42% of fat calories (in a 5% fat diet), they do not develop biochemical EFAD (Table 6). Furthermore, groups without biochemical essential fatty acid deficiency have minimal to no fat in the liver as determined by microscopic analysis of liver sections (Data not shown). This is in contrast to all of the other groups. All groups gained weight equally and did not develop dermatitis. Taken together, these data demonstrate that DHA and AA alone are the essential fatty acids.

References (Example 2)

1. Dorney S F, Ament M E, Berquist W E, Vargas J H, Hassall E. Improved survival in very short small bowel of infancy with use of long-term parenteral nutrition. *J Pediatr*. October 1985; 107(4):521-525.
2. Freund H R. Abnormalities of liver function and hepatic damage associated with total parenteral nutrition. *Nutrition*. January-February 1991; 7(1):1-5; discussion 5-6.
3. Gura K M, Lee S, Valim C, et al. Safety and efficacy of a fish-oil-based fat emulsion in the treatment of parenteral nutrition-associated liver disease. *Pediatrics*. March 2008; 121(3):e678-686.
4. Alwayn I P, Gura K, Nose V, et al. Omega-3 fatty acid supplementation prevents hepatic steatosis in a murine model of nonalcoholic fatty liver disease. *Pediatr Res*. March 2005; 57(3):445-452.
5. Javid P J, Collier S, Richardson D, et al. The role of enteral nutrition in the reversal of parenteral nutrition-associated liver dysfunction in infants. *J Pediatr Surg*. June 2005; 40(6):1015-1018.
6. Zamir O, Nussbaum M S, Bhadra S, Subbiah M T, Rafferty JF, Fischer J E. Effect of enteral feeding on hepatic steatosis induced by total parenteral nutrition. *JPEN J Parenter Enteral Nutr*. January-February 1994; 18(1):20-25.
7. Wales P W, de Silva N, Kim J H, Lecce L, Sandhu A, Moore A M. Neonatal short bowel syndrome: a cohort study. *J Pediatr Surg*. May 2005; 40(5):755-762.
8. Carter B A, Shulman R J. Mechanisms of disease: update on the molecular etiology and fundamentals of parenteral nutrition associated cholestasis. *Nat Clin Pract Gastroenterol Hepatol*. May 2007; 4(5):277-287.
9. Carter B A, Taylor O A, Prendergast D R, et al. Stigmasterol, a soy lipid-derived phytosterol, is an antagonist of the bile acid nuclear receptor FXR. *Pediatr Res*. September 2007; 62(3):301-306.
10. Gura K M, Duggan C P, Collier S B, et al. Reversal of parenteral nutrition-associated liver disease in two infants with short bowel syndrome using parenteral fish oil: implications for future management. *Pediatrics*. July 2006; 118(1):e197-201.
11. Gura KM, Parsons SK, Bechard L J, et al. Use of a fish oil-based lipid emulsion to treat essential fatty acid deficiency in a soy allergic patient receiving parenteral nutrition. *Clin Nutr.* October 2005; 24(5):839-847.
12. Innis S M. Perinatal biochemistry and physiology of long-chain polyunsaturated fatty acids. *J Pediatr.* October 2003; 143(4 Suppl):S1-8.
13. Jeppesen P B, Hoy C E, Mortensen P B. Essential fatty acid deficiency in patients receiving home parenteral nutrition. *Am J Clin Nutr.* July 1998; 68(1):126-133.
14. Holman R. Essential fatty acid deficiency. *Prog Chem Fats Other Lipids.* 1971; 9:275-348.
15. Smit E N, Muskiet F A, Boersma E R. The possible role of essential fatty acids in the pathophysiology of malnutrition: a review. *Prostaglandins Leukot Essent Fatty Acids.* October 2004; 71(4):241-250.
16. Farrell P M, Gutcher G R, Palta M, DeMets D. Essential fatty acid deficiency in premature infants. *Am J Clin Nutr.* August 1988; 48(2):220-229.
17. Holman R T. The ratio of trienoic: tetraenoic acids in tissue lipids as a measure of essential fatty acid requirement. *J Nutr. March* 1960; 70:405-410.
18. Innis S M. Essential fatty acids in growth and development. *Prog Lipid Res.* 1991; 30(1):39-103.
19. Bjerve K S, Fischer S, Alme K. Alpha-linolenic acid deficiency in man: effect of ethyl linolenate on plasma and erythrocyte fatty acid composition and biosynthesis of prostanoids. *Am J Clin Nutr. October* 1987; 46(4):570-576.
20. Bjerve K S, Fischer S, Wammer F, Egeland T. alpha-Linolenic acid and long-chain omega-3 fatty acid supplementation in three patients with omega-3 fatty acid deficiency: effect on lymphocyte function, plasma and red cell lipids, and prostanoid formation. *Am J Clin Nutr.* February 1989; 49(2):290-300.
21. Bjerve K S, Mostad I L, Thoresen L. Alpha-linolenic acid deficiency in patients on long-term gastric-tube feeding: estimation of linolenic acid and long-chain unsaturated n-3 fatty acid requirement in man. *Am J Clin Nutr. January* 1987; 45(1):66-77.
22. Mohrhauer H, Holman R T. The Effect of Dose Level of Essential Fatty Acids Upon Fatty Acid Composition of the Rat Liver. *J Lipid Res.* April 1963; 4:151-159.
23. Javid P J, Greene A K, Garza J, et al. The route of lipid administration affects parenteral nutrition-induced hepatic steatosis in a mouse model. *J Pediatr Surg.* September 2005; 40(9):1446-1453.
24. Strijbosch RAM, Lee S, Arsenault D A, et al. Fish oil prevents essential fatty acid deficiency and enchances growth: clinical and biochemical implications. *Metabolism Clinical and Experimental.* 2008;(in press).

Example 3

Increased AA Produces Liver Injury and Mortality

Experiments in mice were performed in order to investigate the results of consumption of increased arachidonic acid with respect to DHA:AA ratios. Mice were fed as indicated below in Table 7, for 19 days, and monitored for % body weight gain, mortality (ALT), liver injury (as indicated by increased alkaline phosphatase levels), and growth rate. Histology was also used to confirm liver injury in the mice. Results are presented in Table 7 below:

TABLE 7

Effect of increased DHA:AA ratios in the diet

| Group (n = 5) | Mortality | % Body Wt gained | ALT (Mean ± SD) | AP (Mean ± SD) | Notes |
|---|---|---|---|---|---|
| Control Chow | 0% | 7.2 | 28.4 ± 8.0 | 113.6 ± 9.5 | Normal growth |
| 2.1% AA + 0% DHA | 60% | 1.6 | 48.0 ± 20.9 | 142 ± 26.9 | 1 mouse died day# 4, 2 mice died day#6 |
| 2% AA + 0.1% DHA | 40% | 12.1 | 103 ± 111.7 | 157.0 ± 18.4 | 2 mice died day#6 |

Figure 13:
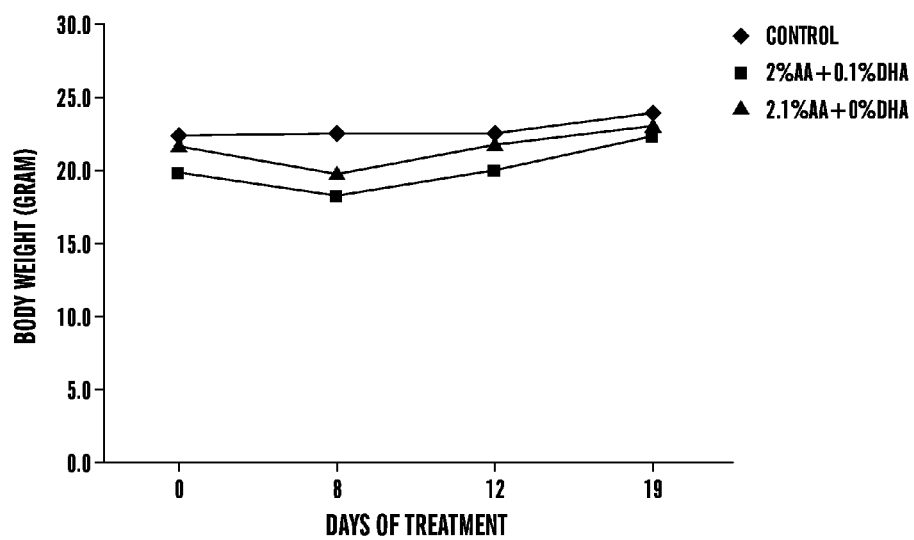
FIG. 13 is a line graph of the body weight of mice following the indicated days of treatment of control chow, 2% AA+0.1% DHA, or 2.1% AA+0% DHA.

Animals treated with increased ratios of AA had increased mortality and liver injury (ALT and alkaline phosphatase). Growth rates were also lower in elevated AA animals than normal controls (Table 7, and FIG. 13). Histology performed on the respective livers confirmed the liver injury. A diet of 2% AA and 0.1% DHA resulted in moderated midzone steatosis in the examined liver sections. A diet of 2.1% AA with 0% DHA resulted in mild apoptosis and moderate necrosis in comparably obtained and prepared liver sections. Both sets of results were obtained by comparison to comparably obtained and prepared liver sections from normal healthy control mice who were fed control chow throughout the study.

The caloric ratio of DHA:AA in these experiments was around 1:1. These results are the first indication that intake of amounts of arachidonic acid which are too high (e.g. in ratios that are 1:1 omega-3 fatty acids such as DHA:AA), are harmful to an individual. These results can be extrapolated to high levels of arachidonic acid precursors as well. This data further supports the hypothesis that amounts of arachidonic acid should be limited in a healthy, non-inflammatory diet.

The invention claimed is:

1. A dietary formulation for total enteral or parenteral nutrition or a dietary supplement in the form of food oil that is suitable for oral administration, comprising:
   from about 2% to about 60% by calories of a $C_{20}$ or longer omega 3 fatty acid;
   from about 0.05% to about 1% by calories of arachidonic acid; and
   wherein the formulation or supplement provides less than 1% of total calories from linoleic acid and alpha-linolenic acid; and
   wherein the ratio of $C_{20}$ or longer omega 3 fatty acid to arachidonic acid is from about 10:1 to about 40:1; and
   wherein all said fatty acids in said formulation or supplement provide from 5 to 60% of the total calories of said dietary formulation or supplement.

* * * * *